United States Patent
Buynak et al.

(10) Patent No.: US 6,916,801 B2
(45) Date of Patent: Jul. 12, 2005

(54) 7-ALKYLIDENE-3-SUBSTITUTED-3-CEPHEM-4-CARBOXYLATES AS β-LACTAMASE INHIBITORS

(75) Inventors: John D. Buynak, Dallas, TX (US); Lakshminarayana Vogeti, Dallas, TX (US)

(73) Assignee: Alamx, LLC, Tucson, AZ (US)

( * ) Notice: Subject to any disclaimer, the term of this patent is extended or adjusted under 35 U.S.C. 154(b) by 0 days.

(21) Appl. No.: 10/202,405

(22) Filed: Jul. 24, 2002

(65) Prior Publication Data

US 2003/0092696 A1 May 15, 2003

Related U.S. Application Data

(60) Provisional application No. 60/307,403, filed on Jul. 24, 2001.

(51) Int. Cl.[7] ................... C07D 501/59; C07D 501/22; C07D 501/20; A61K 31/545; A61P 31/04
(52) U.S. Cl. .................. 514/200; 514/202; 514/203; 514/204; 514/206; 514/208; 540/215; 540/222; 540/224; 540/225; 540/226; 540/227; 540/229
(58) Field of Search ................... 514/206, 208, 514/204, 203, 202, 200; 540/215, 222, 224, 225, 227, 229

(56) References Cited

U.S. PATENT DOCUMENTS

| | | | |
|---|---|---|---|
| 4,053,468 A | 10/1977 | Holden | 544/30 |
| 4,356,174 A | 10/1982 | Barth | 424/114 |

(Continued)

FOREIGN PATENT DOCUMENTS

| | | | |
|---|---|---|---|
| DE | 2708219 | 9/1977 | ......... C07D/501/04 |
| EP | 0041047 | 12/1981 | ......... C07D/499/00 |
| EP | 0050805 | 5/1982 | ......... C07D/499/00 |

(Continued)

OTHER PUBLICATIONS

John D. Buynak, et al Org. Lett.; 2001; 3(19) pp 2953–2956 Web Release Date: Aug. 30, 2001.*
Buynak et al, Bioorganic & Medicinal Chemistry Letters vol. 12, ™12, Jun. 17, 2002, Pp 1663–1666 Available online Apr. 24, 2002.*

(Continued)

Primary Examiner—Mark L. Berch
(74) Attorney, Agent, or Firm—Schwegman, Lundberg, Woessner & Kluth, P.A.

(57) ABSTRACT

The invention provides compounds of formula (I):

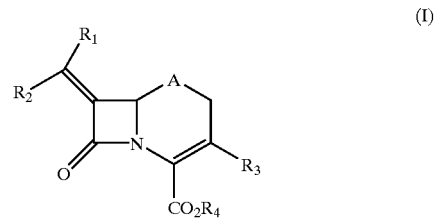

(I)

wherein: $R_1$–$R_4$ and A have any of the values defined in the specification, and their pharmaceutically acceptable salts, are useful for inhibiting β-lactamase enzymes, for enhancing the activity of β-lactam antibiotics, and for treating β-lactam resistant bacterial infections in a mammal. The invention also provides pharmaceutical compositions, processes for preparing compounds of formula (I), wherein $R_1$ and $R_2$ are each independently hydrogen, $(C_1-C_{10})$alkyl, $(C_2-C_{10})$alkenyl, $(C_2-C_{10})$alkenyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$; $R_3$ is hydrogen, halo, aryl, heteroaryl, —S(O)$_n$R$_h$, or —CH=CHC(=O)NR$_m$R$_p$; $R_4$ is hydrogen; A is thio, sulfinyl, or sulfonyl; and intermediates useful for the synthesis of compounds of formula (I).

26 Claims, 6 Drawing Sheets

U.S. PATENT DOCUMENTS

| | | | |
|---|---|---|---|
| 4,512,999 A | 4/1985 | Adam-Molina et al. | 514/192 |
| 4,559,157 A | 12/1985 | Smith et al. | 252/90 |
| 4,608,392 A | 8/1986 | Jacquet et al. | 514/844 |
| 4,820,508 A | 4/1989 | Wortzman | 424/59 |
| 4,826,833 A | 5/1989 | Chen | 514/192 |
| 4,861,768 A | 8/1989 | Torii et al. | 514/195 |
| 4,912,213 A | 3/1990 | Taniguchi et al. | 540/310 |
| 4,938,949 A | 7/1990 | Borch et al. | 424/10 |
| 4,992,478 A | 2/1991 | Geria | 514/782 |
| 5,597,817 A | 1/1997 | Buynak et al. | 514/200 |
| 5,629,306 A | 5/1997 | Buynak et al. | 514/206 |
| 5,637,579 A | 6/1997 | Hubschwerlen et al. | 514/192 |
| 5,681,563 A | 10/1997 | Buynak et al. | 424/114 |
| 5,760,027 A | 6/1998 | Buynak et al. | 514/200 |
| 6,156,745 A | 12/2000 | Buynak et al. | 514/192 |

FOREIGN PATENT DOCUMENTS

| | | | | |
|---|---|---|---|---|
| EP | 0150984 | 8/1985 | | C07D/449/00 |
| EP | 0170192 | 2/1986 | | A61K/31/43 |
| EP | 0367606 | 5/1990 | | C07D/499/86 |
| EP | 0043546 | 1/1992 | | C07D/501/00 |
| GB | 2043639 | 10/1980 | | C07D/499/00 |
| JP | 55-136288 | 10/1980 | | C07D/501/00 |
| JP | 57-99590 | 6/1982 | | C07D/499/00 |
| JP | 58-59990 | 4/1983 | | C07D/499/00 |
| JP | 61-109791 | 5/1986 | | C07D/499/00 |
| JP | 62-198687 | 9/1987 | | C07D/499/00 |
| JP | 64-66189 | 3/1989 | | C07D/499/00 |
| JP | 7-82273 | 3/1995 | | C07D/499/86 |
| WO | WO-96/17849 | 6/1996 | | C07D/501/20 |
| WO | WO-98/24793 | 6/1998 | | C07D/501/00 |
| WO | WO-00/63213 | 10/2000 | | C07D/501/00 |
| WO | WO-03/020732 | 3/2003 | | C07D/501/00 |

OTHER PUBLICATIONS

Abd El–Nabi, H. A., "Novel Heterocycles: A convenient Synthesis of Pyrrolo [2,3–d]pyrazole; Cycloaddion reaction of N–aryl(methyl)pyrrol–2,3–Diones to diazomethane and olefins", *Tetrahedron*, 53(5), (Feb. 1997),1813–1822.

Adam, Solange, "Synthesis of Methylene (R)–6–acetonylidene–3–methyl–7–oxo–4–thia–1– azabicyclo [3.2.0] hept–2–ene–carboxylate pivalate", *Heterocycles*, 22(7), Columbus, Ohio, U.S.,(1984),1509–1512.

Arisawa, M., et al., "6–Acetylmethylenepenicillanic Acid (Ro 15–1903), A Potent B–Lactamasae Inhibitor. I. Inhibition of Chromosomally and R–Factor–Mediated B–Lactamases", *The Journal of Antibiotics*, 35(11), (Nov. 1982), 1578–1583.

Beharry, Zanna, et al., "Penicillin–Derived Inhibitors of the Class A B–Lactamase from *Bacillus Anthracis*", *ICAAC Poster* ™ *C1–679*, Chicago, IL, (2003), 6 pgs.

Bennett, I. S., et al., "6–(Substituted Methylene)Penems, Potent Broad Spectrum Inhibitors of Bacterial B–Lactamse. .V. Chiral 1,2,3–Triazolyl Derivatives", *The Journal of Antibiotics*, 44(9), (Sep. 1991),969–978.

Billups, W. E., et al., "Generation of Simple Methylenecyclopropenes as Reactive Intermediates", *Tetrahedron*, 37 (1981),3215–3220.

Bitha, P., et al., "6–(1–Hydroxyalkyl)Penam Sulfone Derivatives as Inhibitors of Class A and Class C .beta.–Lactamases I", *Bioorganic & Medicinal Letters*, 9(7), (1999), 991–996.

Bitha, P., et al., "6–(1–Hydroxyalkyl)Penam Sulfone Derivatives as Inhibitors of Class A and Class C .beta.–Lactamases II", *Bioorganic & Medicinal Chemistry Letters*, 9(7), (1999),997–1002.

Black, Jennifer, et al., Detection of Plasmid–Mediated AmpC B–Lactamases (pAmpCs) in Disk Tests Based on B–Lactamase Inhibitors (BLIs) Ro 48–1220. (RO) and LN–2–128 (LN), *43rd ICAAC Poster* ™ *D–258*, (2003), 6 pgs.

Blacklock, Thomas J., et al., "A Versatile Synthesis of 1,1–Dioxo 7–Substituted Cepherms: Preparation of the Human Leukocyte Elastase (HLE) Inhibitor 1,1–Dioxo–trans–7–methoxycephalosporanic Acid tert–Butyl Ester", *J. Org. Chem.*, 54, (1989), 3907–3913.

Brenner, D. G., et al., "6–(Methoxymethylene)penicilanic Acid: Inactivator of RTEM B–Lactamse from *Escherichia coli*", *Biochemistry*, 23(24), (Nov. 20, 1984),5839–5846.

Buynak, John D., et al., "7–Alkylidenecephalosporin Esters as Inhibitors of Human Leukocyte Elastase", *J. Med. Chem.*, 40, (1997),pp. 3423–3433.

Buynak, John D., et al., "A Convenient Method for the Production of 6–Oxopenicillinates and 7–Oxocephalosporinates", *Tetrahedron Letters*, 39, (1998),4945–4946.

Buynak, John D., et al., "a–Alkylidene B–Lactams. 2. A Formal Synthesis of (+)–Carpetimycin A", *J. Org. Chem.*, 51, (1986),1571–1574.

Buynak, John D., et al., "Catalytic Approaches to the Synthesis of B–Lactamase Inhibitors", *Tetrahedron*, 56, (2000), 5709–5718.

Buynak, John D., et al., "Reactions of (Silylamino)phosphines with Epoxides and Episulfides", *J. Org. Chem.*, 49, (1984),1828–1830.

Buynak, John D., et al., "Stille Coupling Approaches to the Stereospecific Synthesis of 7–[(E)–Alkylidene]cephalosporins", *Tetrahedron Letters*, 40, (1999),1281–1284.

Buynak, John D., "Synthesis and biological activity of 7–alkylidenecephems", *J. Med. Chem.*, 38, (1995),1022–1034.

Buynak, John D., et al., "Synthesis and mechanistic evaluation of 7–vinylidenecephem sulfones as B–lactamase inhibitors", *J. of Am. Chem. Soc.*, 116, (1994),10955–10965.

Buynak, John D., et al., "Synthesis and Reactivity of Sulfur and Silyl Substituted a–Alkylidene–B–Lactams", *Tetrahedron Letters*, 26, (1985),5001–5004.

Buynak, J. D., et al., "Synthesis of 6–vinylidenepenams", *The Journal of Organic Chemistry*, 58 (6), (Mar. 12, 1993), 1325–1335.

Buynak, John D., et al., "Synthesis of the First 2', 6 Bridged Penams", *J. Am. Chem. Soc.*, 120, (1998),6846–6847.

Buynak, John D., et al., "The Addition of Chlorosulphonyl Isocyanate to an Allenyl Acetate. The Preparation of a Versatile Intermediate for Antibiotic Synthesis", *J. Chem. Soc., Chem. Commun.*, (1984),948–949.

Buynak, John D., et al., "The Preparation and Use of Metallo–6–vinylidene Penams", *J. Chem. Soc., Chem. Commun.*, (1990),294–296.

Buynak, John D., et al., "The Preparation of the First a–Vinylidene–B–lactams", *J. Chem. Soc., Chem. Commun.*, (1987),735–737.

Buynak, John D., "The Preparation of the First a–Vinylidenepenams", *Tetrahedron Letters*, 29, (1988),5053–5056.

Buynak, J. D., "The Synthesis and Evaluation of 2–Substituted–7–(alkylidene)cephalosporin Sulfones as beta–Lactamase Inhibitors", *Bioorganic & Medicinal Chemistry Letters*, 10, (2000),847–851.

Buynak, J. D., "The Synthesis and Evaluation of 3–Substituted–7–(alkylidene)cephalosporin Sulfones as beta–Lactamase Inhibitors", *Bioorganic & Medicinal Chemistry Letters*, 10, (2000),853–857.

Buynak, John D., "The Synthesis and Evaluation of 6–alkylidene–2'beta–substituted penam sulfones as beta–lactamase inhibitors", *Bioorg. Med. Chem. Lett.*, 9, (Jul. 9, 1999),1997–2002.

Buynak, J. D., et al., "The Synthesis and Lactamase Inhibitory Activity of 6–(Carboxymethylene) Pencillins and 7–(Carboxymethylene)Cephalosporins", *Bioorganic & Medicinal Chemistry Letters*, 5 (14), (1995),1513–1518.

Chen, Y. L., et al., "Synthesis of a Potent B–Lactamase Inhibitor–1, 1–Dioxo–6–(2–Pyridyl)Methylenepenicillanic Acid and its Reaction with Sodium methoxide", *Tetrahedron Letters*, 27 (30), (1986),3449–3452.

Crichlow, G. V., "Inhibition of Class C beta–Lactamases: Structure of a Reaction Intermediate with a Cephem Sulfone", *Biochemistry*, 40, (2001),6233–6239.

De Meester, Patrice, et al., "3–[(Z)–p–Chlorophenylthio–(E)–trimethylsilylmethylidene]–1, 4–dimethyl–4–trimethylsilylazetidin–2–one: an a–Alkylidene–B–lactam", *Acta Cryst.*, C42, (1986),1260–1262.

Dininno, Frank, et al., "Aldol Condensations of Regiospecific Penicillanate and Cephalosporanate Enolates. Hydorxyethylation at C–6 and C–7", *J. Org. Chem.*, 42, (1977),2960–2965.

Farina, Vittorio, et al., "A General Route to 3–Functionalized 3–Norcephalosporins", *J. Org. Chem.*, 54, (1989), 4962–4966.

Gutsche, C. D., "The Chemistry of Carbonyl Compounds", *Prentice–Hall, Englewood Cliffs, NY*, 46–47.

Haebich, D., et al., "Inhibitors of .beta. –lactamases. 2. Synthesis of 6–sulfonylmethylene–, 6–sulfinylmethylene– and spiropyrazoline– penicillanic acids", *Chemical Abstracts Service*, 24(2), Columbus, Ohio, U.S., (1986), 289–296.

Hagiwara, D., et al., "An Efficient Synthesis of 6–Oxopenicillanic and 7–Oxocephalosporanic Acid Derivatives", *Journal of Chemical Society Chemical Communications*, 11, (Jun. 1, 1982),578–579.

Kant, J., et al., "Diastereoselective Addition of Grignard Reagents to Azetidine–2,3–dione: Synthesis of Novel Taxol Analogues", *Tetrahedron Letters*, 37 (36), (Sep. 2, 1996), 6495–6498.

Kollenz, G., et al., "Reactions of Cyclic Oxalyl Compounds—38. New Isoindigoide Dyes from Heterocyclic 2,3–Diones—Synthesis and Thermal Rearrangement", *Tetrahedron*, 52(15), (Apr. 1996),5427–5440.

Mak, Ching–Pong, et al., "Chemicl Studies on the Transformation of Penicillins I. Synthesis of Cyclic Disulfides and Thiosulfinates Related to Asparagusic Acid", *Heterocycles*, 27(2), Columbus, Ohio, U.S., (1988),331–337.

Martin, Micahel G., et al., "Epoxides as Alkene Protecting Groups. A Mild and Efficient Deoxygenation", *Tetrahedron Letters*, 25 (3), (1984),pp. 251–254.

Miyashita, Kazuyuki, et al., "Design, Synthesis, and Evaluation of a Potent Mechanism–Based Inhibitor for the TEM B–Lactamase with Implications for the Enzyme Mechanism", *J. Am. Chem. Soc.*, 117, (1995),11055–11059.

Murata, Y., et al., "Acute, Subacute, and Chronic Parenteral Toxicities of disodium.alpha.–sulfobenzylpencillin (Sulfocillin) in Mice, Dogs, and Rats", *Chemical Abstracts Service*, 30(2), Columbus, Ohio, U.S., (1971),262–283.

Palomo, C., et al., "New Synthesis of a–Amino Acid N–Carboxy Anhydrides through Baeyer–Viliger Oxidation of a–keto B–Lactams", *The Journal of Organic Chemistry*, 59 (11), (Jun. 3, 1994),3123–3130.

Roberts, John D., et al., "Basic Principles of Organic Chemistry", *Benjamin, NY*, (1964),405, 537.

Siriwardane, Upali, et al., "1,1, 3'–Trimethyl–3'–(trimethylsilyl)perhydroazetidino[1,2–c] [1,3]oxazine–5–spiro–2'–oxiran–6–one, a Novel B–Lactam", *Acta Cryst.*, C45, (1989),531–533.

Siriwardane, Upali, et al., "4–Benzyl–3–(ethenylidene)azetidin–2–one: the First a–Vinylidene–B–lactam", *Acta Cryst.*, C43, (1987),2242–2243.

Siriwardane, Upali, et al., "4–Methyl–3–{(Z)–methyl [(E)–dimethyl(phenyl)silyl]methylidene}azetidin–2–one: an a–Alkylidene–B–lactam", *Acta Cryst.*, C44, (1988),391–393.

Van Der Veen, J. M., et al., "Synthesis of Azetidine–2,3–diones (a–Keto B–Lactams) via 3–(Phenylthio)–2–azetidinones", *The Journal of Organic Chemistry*, 54 (24), (Nov. 24, 1989),5758–5762.

Volkmann, R. A., et al., "Efficient Preparation of 6,6–Dihalopenicillanic Acids. Synthesis of Penicillanic Acid S,S–Dioxide (Sulbactam)", *J. Org. Chem.*, 47, (1982),3344–3345.

* cited by examiner

8a R = SMe
8b R = SPh

10a R = SO₂Me
10b R = SO₂Ph

11a R = SO₂Me
11b R = SO₂Ph

15

16a R = cyclopropyl
16b R = OTBS

17a R = cyclopropyl
17b R = OTBS

18a R = cyclopropyl
18b R = OH

7-ALKYLIDENE-3-SUBSTITUTED-3-CEPHEM-4-CARBOXYLATES AS β-LACTAMASE INHIBITORS

PRIORITY OF INVENTION

This application claims priority under 35 U.S.C. 119(e) from U.S. Provisional Application No. 60/307,403, filed Jul. 24, 2001, which application is incorporated herein by reference.

STATEMENT OF GOVERNMENT RIGHTS

This invention was made, at least in part, with a grant from the Government of the United States of America (Grant No. I R41 A148997-01 from the National Institutes of Health). The Government may have certain rights to the invention.

BACKGROUND OF THE INVENTION

The most important mechanism of microbial resistance to β-lactam antibiotics is the bacterial production of β-lactamases, enzymes which hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C, and D based on amino acid sequence. Class A, which includes RTEM and the β-lactamase of *Staphylococcus aureus*, class C, which includes the lactamase derived from P-99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of Gram-negative bacteria and have molecular weights of approximately 39 kDa. The recently recognized class D enzymes exhibit a unique substrate profile which differs significantly from both class A and class C.

The class C cephalosporinases, in particular, are responsible for the resistance of gram negative bacteria to a variety of both traditional and newly designed antibiotics. The Enterobacter species, which possesses a class C enzyme, is now the third greatest cause of nosocomial infections in the United States. This class of enzymes often has poor affinities for inhibitors of the class A enzymes, such as clavulanic acid, a commonly prescribed inhibitor, and to common in vitro inactivators, such as 6-β-iodopenicillanate.

One strategy for overcoming this rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is the product sold under the trademark AUGMENTIN (amoxicillin, clavulanate potassium), which contains the antibiotic amoxicillin and the β-lactamase inhibitor, clavulanate potassium.

There is a continued need for novel β-lactamase inhibitors, and in particular, for β-lactamase inhibitors that can be coadministered with a β-lactam antibiotic.

SUMMARY OF THE INVENTION

The invention also provides a compound of formula (I):

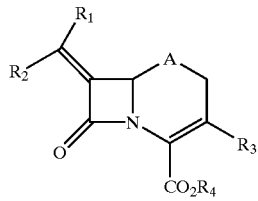

(I)

wherein:
$R_1$ and $R_2$ are each independently hydrogen, $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, $(C_1-C_{10})$alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

$R_3$ is hydrogen, halo, aryl, heteroaryl, —S(O)$_n$R$_h$, or —CH=CHC(=O)NR$_m$R$_p$;

$R_4$ is hydrogen;

A is thio, sulfinyl, or sulfonyl;

each n is independently 0, 1, or 2;

each R$_e$ is independently hydrogen, or $(C_1-C_{10})$alkyl;

each R$_f$ and R$_g$ is independently hydrogen, $(C_1-C_{10})$alkyl, $(C_1-C_{10})$alkoxy, phenyl, benzyl, phenethyl, $(C_1-C_{10})$alkanoyl, or —C(=O)NO; wherein O and the N atom to which it is attached forms a ring containing from 2–20 carbon atoms optionally containing a nitrogen atom in the ring, —NR$_e$—;

each R$_h$ is independently $(C_1-C_{10})$alkyl, or aryl; and

R$_m$ is hydrogen, and R$_p$ is NH$_2$, OH, $(C_2-C_{10})$cycloalkyl, or —$(C_2-C_{10})$alkyl-NH$_2$; or R$_m$ and R$_p$ together with the nitrogen to which they are attached form a piperidine, morpholine, thiomorpholine, pyrrolidine, or piperazine ring, wherein the piperazine is substituted at the 4-position with hydrogen or a $(C_1-C_{10})$alkyl;

wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $(C_1-C_{10})$alkanoyl, $(C_1-C_{10})$alkanoyloxy, or $(C_1-C_{10})$alkoxycarbonyl of $R_1$ or $R_2$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, —NR$_h$R$_i$, or —S(O)$_n$R$_k$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_h$R$_i$, or —S(O)$_n$R$_k$; or a pharmaceutically acceptable salt thereof.

The invention provides a pharmaceutical composition comprising a compound of formula (I), or a pharmaceutically acceptable salt thereof, in combination with a pharmaceutically acceptable diluent or carrier, as well as such a pharmaceutical composition that further comprises a β-lactam antibiotic.

The invention also provides a method comprising inhibiting a β-lactamase by contacting (in vitro or in vivo) the β-lactamase with an effective amount of a compound of formula (I); or a pharmaceutically acceptable salt thereof.

The invention also provides a therapeutic method comprising inhibiting a β-lactamase in a mammal in need of such therapy, by administering an effective inhibitory amount of a compound of formula (I); or a pharmaceutically acceptable salt thereof.

The invention also provides a method comprising enhancing the activity of a β-lactam antibiotic, by administering the β-lactam antibiotic to a mammal in need thereof, in combination with an effective β-lactamase inhibiting amount of a compound of formula (I); or a pharmaceutically acceptable salt thereof.

The invention also provides a method comprising treating a β-lactam resistant bacterial infection in a mammal, by administering an effective amount of a β-lactam antibiotic in combination with an effective β-lactamase inhibiting amount of a compound of formula (I); or a pharmaceutically acceptable salt thereof.

The invention also provides a compound of formula (I) for use in medical therapy (preferably for use in inhibiting a β-lactamase in a mammal, or for treating a β-lactam resistant bacterial infection in a mammal), as well as the use of a compound of formula (I) for the manufacture of a medicament useful for inhibiting a β-lactamase in a human.

The invention also provides processes and intermediates disclosed herein that are useful for preparing β-lactamase inhibitors of formula (I).

Compounds of formula (I) are useful as β-lactamase inhibitors for therapeutic applications. They are also useful as pharmacological tools for in vitro or in vivo studies to investigate the mechanisms of antibiotic resistance, to help identify other therapeutic antibiotic agents or β-lactamase inhibitors, to identify which β-lactamases are being expressed by a given microorganism, or to selectively inhibit one or more β-lactamases in a microorganism.

DETAILED DESCRIPTION

Figure 1:
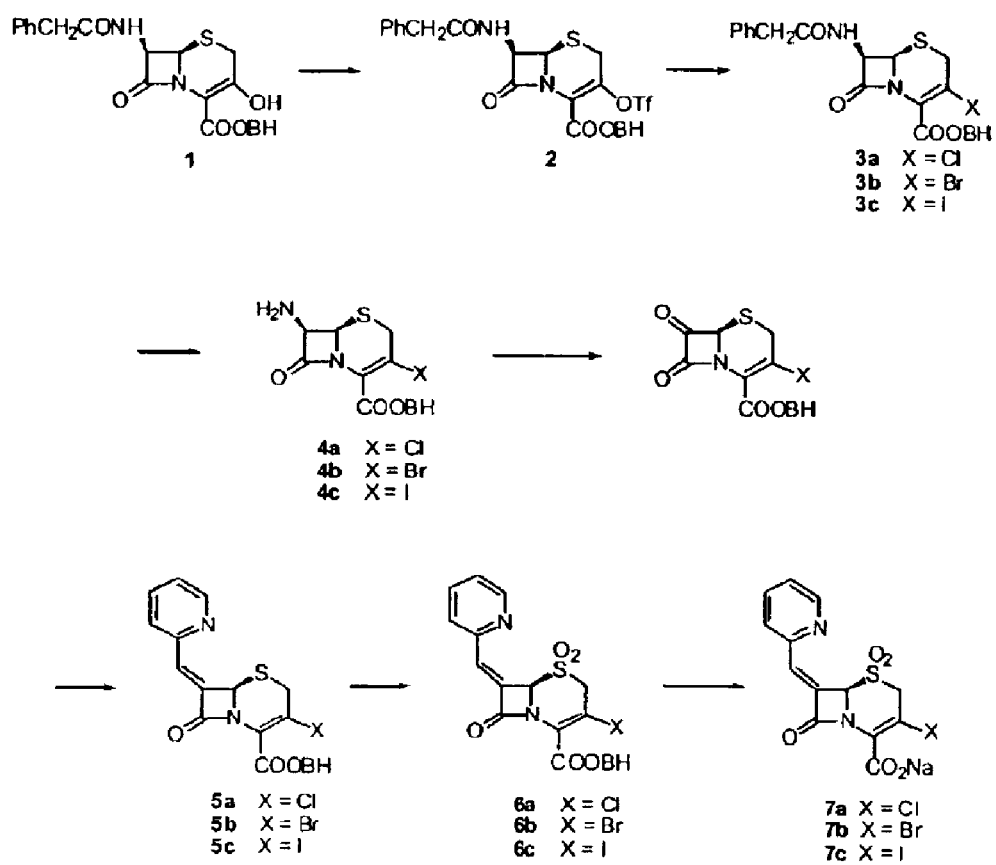
FIGS. 1–6 illustrate the preparation of representative compounds of the invention.

The following definitions are used, unless otherwise described: halo is fluoro, chloro, bromo, or iodo. Alkyl, alkoxy, alkenyl, and the like, denote both straight and branched groups. Aryl denote a phenyl radical, or an ortho-fused bicyclic carbocyclic radical having about nine to ten ring atoms in which at least one ring is aromatic. Heterocycle denotes a 6–10 membered unsaturated or saturated mono-, bi-, or tri-cyclic ring system comprising carbon and 1, 2, 3, or 4 heteroatoms selected from the group consisting of non-peroxide oxygen, sulfur, and N(X) wherein each X is absent or is H, O, ($C_1$–$C_4$)alkyl, phenyl or benzyl. The term "heterocycle" includes "Heteroaryl," which denotes a radical attached via a ring carbon of a monocyclic aromatic ring containing five or six ring atoms consisting of carbon and one to four heteroatoms each selected from the group consisting of non-peroxide oxygen, sulfur, and N(X) wherein each X is absent or is H, O, ($C_1$–$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. A preferred heteroaryl is, for example, a pyridyl radical.

The term "enhancing" the activity of a β-lactam antibiotic means improving or increasing the antibiotic activity of the compared in a statistically measurable and significant manner with respect to the activity demonstrated by the compound in the absence of a compound of the invention.

The letters "BH" or "bhl" represent a benzhydryl ester.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine β-lactamase inhibitory activity using the standard tests described herein, or using other similar tests which are well known in the art.

Specific values listed below for radicals, substituents and ranges, are for illustration only; they do not exclude other defined values or other values within defined ranges for the radicals and substituents.

Specifically, ($C_1$–$C_6$)alkyl can be methyl, ethyl, propyl, isopropyl, butyl, iso-butyl, sec-butyl, pentyl, 3-pentyl, or hexyl; ($C_1$–$C_{10}$)alkyl can be methyl, ethyl, propyl, isopropyl, butyl, iso-butyl, sec-butyl, pentyl, 3-pentyl, hexyl, heptyl, octyl, nonyl, or decyl; ($C_3$–$C_8$)cycloalkyl can be cyclopropyl, cyclobutyl, cyclopentyl, cyclohexyl, cycloheptyl, or cyclooctyl; ($C_1$–$C_{10}$)alkoxy can be methoxy, ethoxy, propoxy, isopropoxy, butoxy, iso-butoxy, sec-butoxy, pentoxy, 3-pentoxy, decyloxy; ($C_1$–$C_6$)alkoxy can be methoxy, ethoxy, propoxy, isopropoxy, butoxy, iso-butoxy, sec-butoxy, pentoxy, 3-pentoxy, or hexyloxy; ($C_2$–$C_{10}$)alkenyl can be vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; ($C_2$–$C_{10}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; ($C_1$–$C_{10}$) alkanoyl can be acetyl, propanoyl, butanoyl, pentanoyl, hexanoyl, heptanoyl, octanoyl, nonanoyl, or decanoyl; ($C_1$–$C_{10}$)alkoxycarbonyl can be methoxycarbonyl, ethoxycarbonyl, propoxycarbonyl, isopropoxycarbonyl, butoxycarbonyl, pentoxycarbonyl, hexyloxycarbonyl, heptyloxycarbonyl, octyloxycarbonyl, nonyloxycarbonyl or decyloxycarbonyl; ($C_1$–$C_{10}$)alkanoyloxy can be formyloxy, acetoxy, propanoyloxy, butanoyloxy, isobutanoyloxy, pentanoyloxy, hexanoyloxy, heptanoyloxy, octanoyloxy, nonanoyloxy, or decanoyloxy; aryl can be phenyl, indenyl, or naphthyl; heterocycle can be benztriazolyl, triazinyl, oxazoyl, isoxazolyl, oxazolidinoyl, isoxazolidinoyl, thiazolyl, isothiazoyl, pyrazolyl, imidazolyl, pyrrolyl, pyrazinyl, pyridinyl, morpholinyl, quinolinyl, isoquinolinyl, indolyl, pyrimidinyl, piperidinyl, pyrrolidinyl, morpholinyl, thiomorpholinyl, or piperazinyl; and heteroaryl can be, for example, furyl, imidazolyl, triazolyl, triazinyl, oxazoyl, isoxazoyl, thiazolyl, isothiazoyl, pyrazolyl, pyrrolyl, pyrazinyl, tetrazolyl, 1-methyl-1H-tetrazol-5-yl, pyridyl, (or its N-oxide), thienyl, pyrimidinyl (or its N-oxide), indolyl, isoquinolyl (or its N-oxide) or quinolyl (or its N-oxide).

In one embodiment, the invention provides a compound of formula (I):

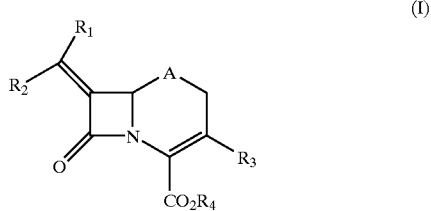

(I)

wherein:

$R_1$ and $R_2$ are each independently hydrogen, $(C_{10}-C_{10})$ alkyl, $(C_2-C_{10})$alkenyl, $(C_2-C_{10})$alkynyl, $(C_3-C_8)$ cycloalkyl, $(C_1-C_{10})$alkoxy, $(C_1-C_{10})$alkanoyl, $(C_1-C_{10})$ alkanoyloxy, $(C_1-C_{10})$alkoxycarbonyl, aryl, heteroaryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

$R_3$ is hydrogen, halo, aryl, heteroaryl, heterocycle, —Sn$(R_5)_3$, —SAr, —S(O)$_n$Ar, —S(O)$_n$R$_h$, —S(O)$_n$NH$_2$, —S(O)$_n$ NHR$_f$, —S(O)$_n$NR$_f$R$_g$, —COOR$_m$, —C(O=)—R$_h$, —C(=O)NR$_f$R$_g$, —CH=NOR$_i$, —CH=CR$_j$R$_k$, or cyano;

$R_4$ is hydrogen, aryl, heterocycle, $(C_1-C_{10})$alkyl, benzyl, phenethyl, -diaryl substituted$(C_1-C_{10})$alkyl, such as —CHAr$_2$ or —CHPh$_2$;

each $R_5$ is independently —$(C_1-C_{10})$alkyl, $(C_1-C_{10})$ alkoxy, phenyl, benzyl, phenethyl;

A is thio, sulfinyl, or sulfonyl;

each n is independently 0, 1, or 2;

each $R_e$ is independently hydrogen, or $(C_1-C_{10})$alkyl;

each $R_f$ and $R_g$ is independently hydrogen, $(C_1-C_{10})$alkyl, $(C_1-C_{10})$alkoxy, phenyl, benzyl, phenethyl, $(C_1-C_{10})$ alkanoyl, or —C(=O)NO; wherein O and the N atom to which it is attached forms a ring containing from 2–20 carbon atoms optionally containing a nitrogen atom in the ring, —NR$_e$—;

each $R_h$ is independently $(C_1-C_{10})$alkyl, phenyl, aryl $(C_1-C_6)$alkyl, heterocycle, or heterocycle$(C_1-C_6)$alkyl;

$R_i$ is hydrogen or $(C_1-C_6)$alkyl; and $R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S)O)$_n$R$_h$;

$R_m$ is —H, —Na, —K, —Li, and like pharmaceutically acceptable salts, —$(C_1-C_{10})$alkyl, —$(C_1-C_{10})$cycloalkyl, benzyl, phenethyl, -diaryl substituted$(C_1-C_{10})$alkyl, such as —CHAr$_2$ or —CHPh$_2$;

wherein any $(C_1-C_{10})$alkyl, $(C_2-C_{10})$alkenyl, $(C_2-C_{10})$ alkynyl, $(C_3-C_8)$cycloalkyl, $(C_1-C_{10})$alkoxy, $(C_1-C_{10})$ alkanoyl, $(C_1-C_{10})$alkanoyloxy, or $(C_1-C_{10})$alkoxycarbonyl of $R_1$, $R_2$, $R_5$, $R_j$ and $R_k$ is optionally substituted with one or more, substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$ alkoxy, $(C_1-C_6)$alkanoyl, $(C_1-C_6)$alkanoyloxy, aryl$(C_1-C_6)$ alkanoyloxy, halo$(C_1-C_6)$alkanoyloxy, heterocycle$(C_1-C_6)$ alkanoyloxy, aryloxy, (heterocycle)oxy, $(C_3-C_8)$cycloalkyl, —COOR$_e$, —C(=O)NR$_f$R$_g$, —OC(=O)NR$_f$R$_g$, —NR$_h$R$_i$, or —S(O)$_n$R$_k$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —COOR$_e$, —C(=O)NR$_f$R$_g$, —OC(=O)NR$_f$R$_g$, NR$_h$R$_i$, or —S(O)$_n$R$_k$ or a pharmaceutically acceptable salt thereof.

Specifically, A is sulfonyl (—SO$_2$—).

Specifically, $R_1$ is aryl, heterocycle, or —COOR$_e$.

Specifically, $R_1$ is 2-pyridyl, or —COOR$_e$.

Specifically, $R_2$ is hydrogen.

Specifically, $R_3$ is hydrogen, halo, aryl, heterocycle, —Sn$(R_5)_3$, —SAr, —S(O)$_n$Ar, —S(O)$_n$R$_h$, —S(O)$_n$NH$_2$, —S(O)$_n$ NHR$_f$, —S(O)$_n$NR$_f$R$_g$, —COOR$_m$, —C(=O)—R$_h$, or —C(=O)NR$_f$R$_g$.

Specifically, $R_3$ is hydrogen, aryl, heteroaryl, —Sn$(R_5)_3$, —SAr, —S(O)$_n$Ar, —S(O)$_n$R$_h$, —S(O)$_n$NH$_2$, —S(O)$_n$ NHR$_f$, or —S(O)$_n$NR$_f$R$_g$.

Specifically, $R_j$ and $R_k$ are each independently hydrogen, cyano, —COOR$_e$, $(C_2-C_{10})$alkenyl, or heteroaryl.

A specific compound of formula (I) is a compound of wherein: $R_1$ and $R_2$ are each independently hydrogen, $(C_1-C_{10})$alkyl, $(C_2-C_{10})$alkenyl, $(C_2-C_{10})$alkynyl, $(C_3-C_8)$ cycloalkyl, $(C_1-C_{10})$alkoxy, $(C_1-C_{10})$alkanoyl, $(C_1-C_{10})$ alkanoyloxy, $(C_1-C_{10})$alkoxycarbonyl, aryl, heteroaryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$; $R_3$ is independently hydrogen, fluoro, —SPh, —SO$_2$Ar, —Sn(CH$_3$)$_3$, or —CH=CH—CO$_2$H; $R_4$ is independently hydrogen, phenyl, heterocycle, $(C_1-C_{10})$alkyl, benzyl, phenethyl, or —CHPh$_2$; A is thio, sulfinyl, or sulfonyl; each n is independently 0, 1, or 2; each $R_e$ is independently hydrogen, or $(C_1-C_{10})$alkyl; each $R_f$ and $R_g$ is independently hydrogen, $(C_1-C_{10})$alkyl, $(C_1-C_{10})$alkoxy, phenyl, benzyl, phenethyl, $(C_1-C_{10})$ alkanoyl, or —C(=O)NR$_f$R$_g$ wherein $R_f$ and $R_g$ form a ring optionally containing a nitrogen atom in the ring —NR$_e$—; each $R_h$ is independently $(C_1-C_{10})$alkyl, phenyl, aryl $(C_1-C_6)$alkyl, heterocycle, or heterocycle$(C_1-C_6)$alkyl; $R_i$ is hydrogen or $(C_1-C_6)$alkyl; and $R_j$ and $R_k$ are each independently hydrogen, halo, cyano, nitro, aryl, heterocycle, $(C_2-C_6)$alkenyl, —COOR$_e$, —C(=O)NR$_f$R$_g$, —OC(=O)NR$_f$R$_g$, NR$_f$R$_g$, or —S(O)$_n$R$_h$; wherein any $(C_1-C_{10})$alkyl, $(C_2-C_{10})$alkenyl, $(C_2-C_{10})$alkynyl, $(C_3-C_8)$ cycloalkyl, $(C_1-C_{10})$alkoxy, $(C_1-C_{10})$alkanoyl, $(C_1-C_{10})$ alkanoyloxy, or $(C_1-C_{10})$alkoxycarbonyl of $R_1$, $R_2$, $R_j$ and $R_k$ is optionally substituted with one or more substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(C_1-C_6)$alkanoyl, $(C_1-C_6)$ alkanoyloxy, aryl$(C_1-C_6)$alkanoyloxy, halo$(C_1-C_6)$ alkanoyloxy, heterocycle$(C_1-C_6)$alkanoyloxy, aryloxy, (heterocycle)oxy, $(C_3-C_8)$cycloalkyl, —COOR$_e$, —C(=O) NR$_f$R$_g$, —OC(=O)NR$_f$R$_g$, NR$_h$R$_i$, or —S(O)$_n$R$_k$; and wherein any aryl is optionally substituted with one or more substituents independently selected from halo, hydroxy, cyano, trifluoromethyl, nitro, trifluoromethoxy, $(C_1-C_6)$ alkyl, $(C_1-C_6)$alkanoyl, $(C_1-C_6)$alkanoyloxy, $(C_1-C_6)$ alkoxycarbonyl, —COOR$_e$, —C(=O)NR$_f$R$_g$, —OC(=O) NR$_f$R$_g$, NR$_h$R$_i$, or —S(O)$_n$R$_k$; or a pharmaceutically acceptable salt thereof.

Another specific compound is a compound wherein one of $R_j$ and $R_k$ is hydrogen and the other is cyano, —COOR$_e$, $(C_2-C_{10})$alkenyl, or heteroaryl.

Another specific compound is a compound wherein $R_j$ is hydrogen or halo, and $R_k$ is cyano, methoxycarbonyl, aminocarbonyl, tert-butoxycarbonyl, 2-pyridyl-N-oxide, nitro, or vinyl.

Another specific compound is a compound wherein A is sulfonyl; $R_1$ is 2-pyridyl, carboxy or tert-butoxy carbonyl; $R_2$ is hydrogen; $R_3$ is hydrogen, fluoro, —SPh, —$SO_2$Ph, —Sn($R_5$)$_3$, or —CH=CH—$CO_2$H; and $R_4$ is hydrogen, —CH$Ar_2$, or a pharmaceutically acceptable salt.

More specifically, $R_j$ and $R_k$ are each independently hydrogen, cyano, 2-(methoxycarbonyl), 2-pyridyl-N-oxide, or vinyl.

Another specific compound is a compound of formula (I) wherein A is sulfonyl (—$SO_2$—); $R_1$ is 2-pyridyl, carboxy or tert-butoxycarbonyl; $R_2$ is hydrogen; and $R_3$ is hydrogen, halo such as fluoro, —SAr such as —SPh, —Sn($R_5$)$_3$, cyano, —S(O)$_n$Ar; —CH=NOR$_i$, or —CH=C$R_jR_k$; or a pharmaceutically acceptable salt thereof.

A more specific compound of formula (I) is a pharmaceutically acceptable salt formed from a carboxylic acid of formula (I) wherein $R_4$ is hydrogen. Most preferred is a salt wherein $R_4$ been replaced with a sodium or potassium ion. The term pharmaceutically acceptable salts also includes poly salts (e.g. di- or tri-salts) of a compound of formula (I).

Processes and novel intermediates useful for preparing compounds of formula (I) are provided as further embodiments of the invention and are illustrated by the following procedures in which the meanings of the generic radicals are as given above unless otherwise qualified.

Representative compounds were prepared as indicated in FIGS. 1 to 6. Commercially available 3-hydroxy-3-cephem 1 was converted to halides 3a, 3b, and 3c by employing the method of Farina (Farina et. al., J. Org. Chem. 54, 4962–4966 (1989)). The phenylacetyl group was removed upon treatment with $PCl_5$ to produce free amines 4a, 4b, and 4c respectively. These were converted to the corresponding 7-oxo-3-cephems and subsequently to the 7-(2'-pyridylmethylidene)-3-cephems 5a, 5b, and 5c. These were readily oxidized to the corresponding sulfones upon treatment with excess mCPBA and the 4-position carboxylate deprotected by treatment with TFA (followed by neutralization with bicarbonate) to produce the corresponding sodium salts 7a, 7b, and 7e.

Figure 2:
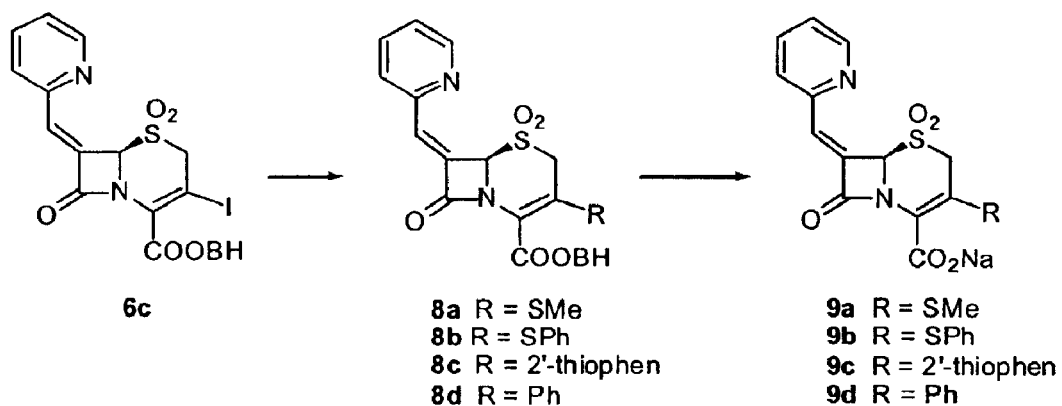
Figure 3:
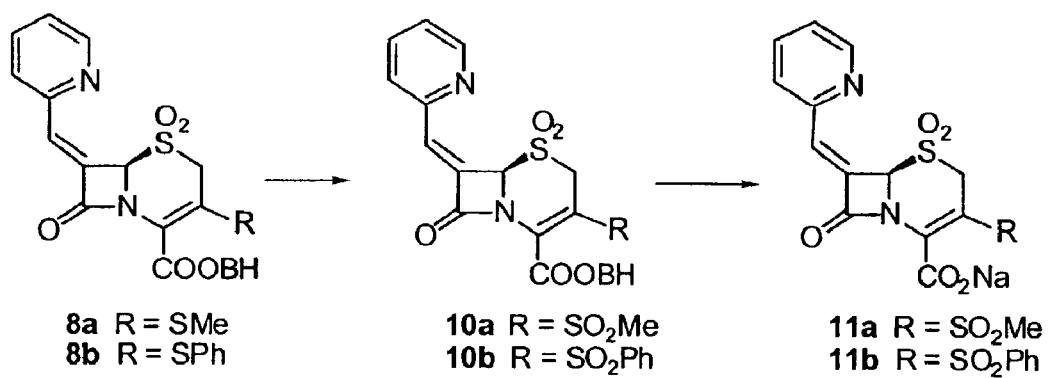

Iodide 6c was also useful in producing other C3 substituted analogs through Stille Coupling reactions with selected organostannanes as shown in FIG. 2. Such reactions resulted in the production of representative C3-sulfides, aryl, and heteroaryl compounds which were also deprotected as shown in FIG. 2. The C3 sufides 8a and 8b could also be oxidized to the corresponding C3 sulfonyl compounds and deprotected to produce the corresponding sodium salts as shown in FIG. 3.

Figure 4:
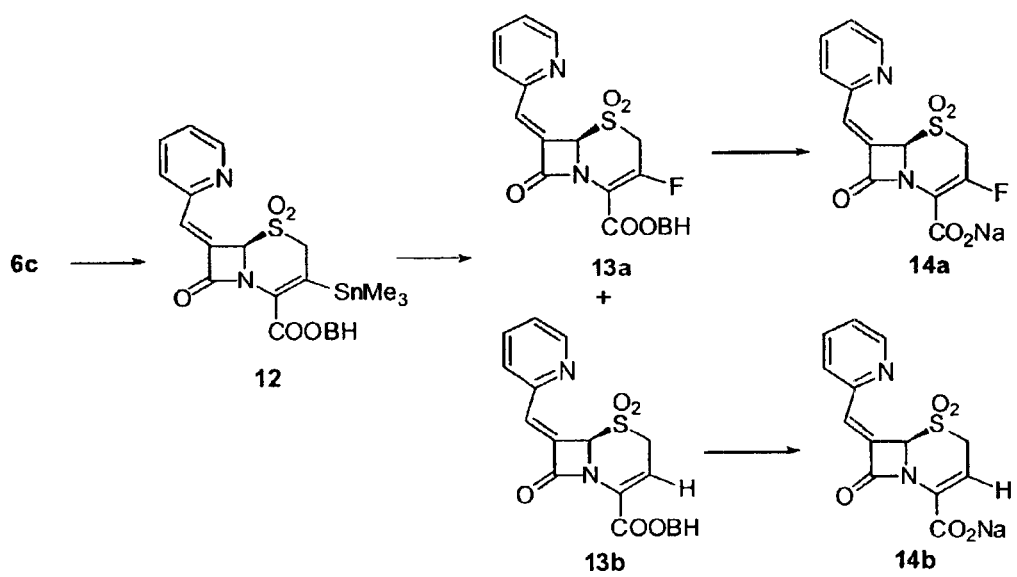
Figure 5:
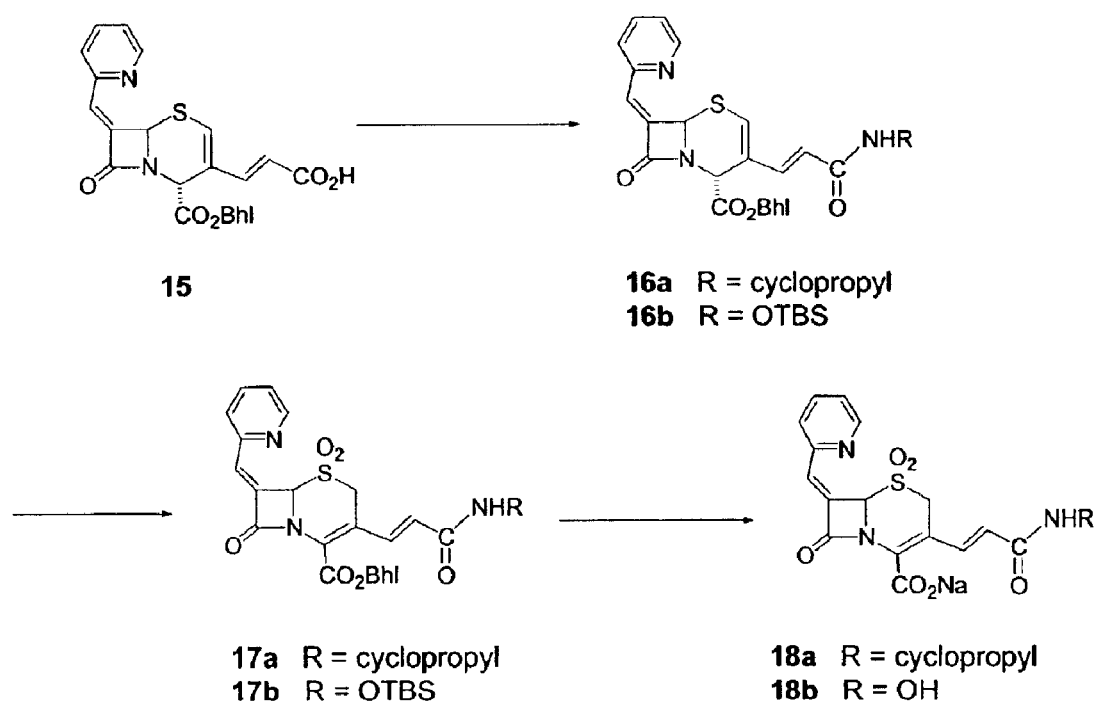
Figure 6:
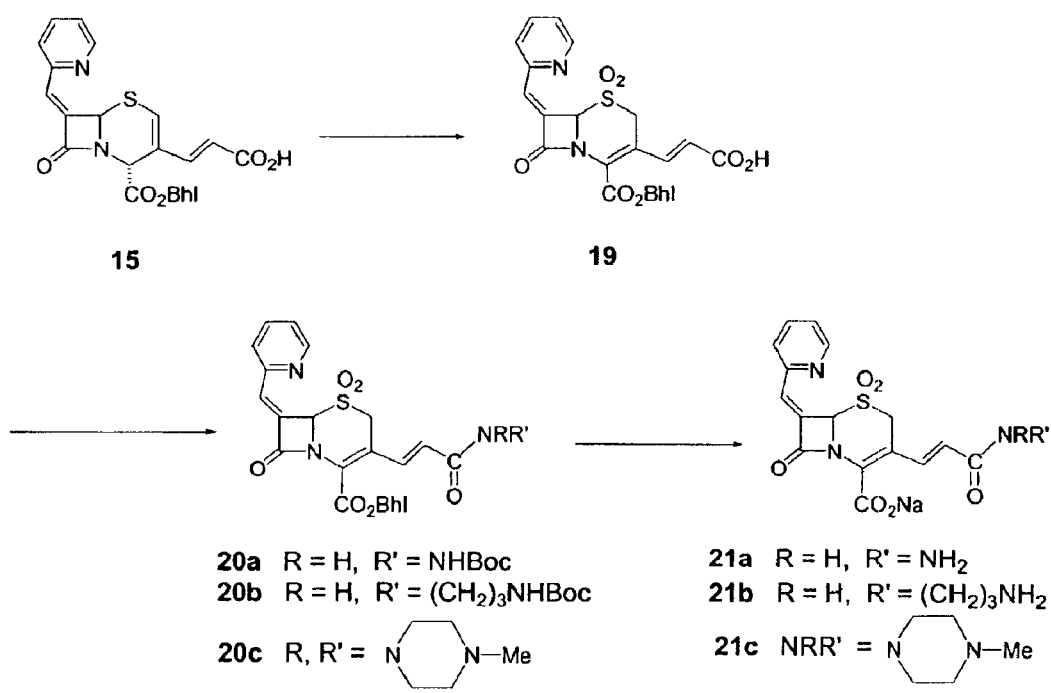

Additionally, compound 6c was converted to the C3 stannylated analog as shown in FIG. 4. This compound was utilized to generate the C3 fluorinated (14a) and C3 unsubstituted (14b) compounds as shown.

Using procedures similar to those described herein, as well as standard synthetic techniques, the compounds of formula (I) can be prepared.

Pharmaceutically acceptable salts of compounds of formula (I) wherein $R_4$ has been replaced with a pharmaceutically acceptable cation (e.g. a sodium or potassium ion) can conveniently be prepared from a corresponding compound of formula (I) wherein $R_4$ is hydrogen, by reaction with a suitable base.

A useful intermediate for preparing a compound of formula (I), wherein $R_4$ is hydrogen, is a corresponding compound wherein $R_4$ has been replaced with a suitable removable carboxy protecting group. Such protecting groups are well known in the art, for example, see Greene, T. W.; Wutz, P. G. M. "Protecting Groups In Organic Synthesis" second edition, 1991, New York, John Wiley & Sons, Inc. Preferred protecting groups include ($C_1$–$C_{10}$)alkyl, ($C_2$–$C_{10}$)alkenyl, ($C_3$–$C_8$)cycloalkyl, ($C_2$–$C_{10}$)alkynyl, aryl, benzyl, or benzhydryl. Thus the invention provides compounds of formula (I) wherein $R_1$, $R_2$, and $R_3$ have any of the values, specific values, or preferred values defined herein, and wherein $R_4$ is ($C_1$–$C_{10}$)alkyl, ($C_2$–$C_{10}$)alkenyl, ($C_3$–$C_8$)cycloalkyl, ($C_2$–$C_{10}$)alkynyl, aryl, benzyl, and benzhydryl.

Another useful intermediate for preparing a compound of formula (I), is a compound of formula (I) wherein $R_3$ is a tin containing group, e.g., a group of formula —Sn(R)$_3$ wherein each R is ($C_1$–$C_6$)alkyl. Accordingly, the invention also provides a compound of formula (I) wherein $R_1$, $R_2$, and $R_4$ have any of the values described herein, and wherein $R_3$ is —Sn(R)$_3$ wherein each R is ($C_1$–$C_6$)alkyl.

A compound of formula (I) wherein A is sulfonyl (—$SO_2$—) can be prepared by oxidation of a corresponding compound of formula (I) wherein A is thio (—S—), for example, by using meta-chloroperbenzoic acid (mCPBA).

A compound of formula (I) wherein A is sulfinyl (—SO—) can be prepared by oxidation of a corresponding compound of formula (I) wherein A is thio (—S—), using one equivalent of an acceptable oxidizing agent, for example, mCPBA. A compound of formula (I) wherein $R_3$ is hydrogen, aryl, heteroaryl, or —S$R_h$, can be prepared by combining a corresponding compound of formula (I) wherein $R_3$ is halo, with an organostannane of formula ($R_a$)$_3$Sn—$R_3$ and a catalyst, to provide the compound of formula (I). Accordingly, the invention also provides a method of preparing a compound of formula (I) wherein $R_3$ is hydrogen, aryl, heteroaryl, or —S$R_h$, and $R_4$ is hydrogen; comprising: combining a corresponding compound of formula (I) wherein $R_3$ is halo and $R_4$ is a protecting group, with an organostannane of formula ($R_a$)$_3$Sn—$R_3$ and a catalyst, to provide a compound of formula (I) wherein $R_3$ is hydrogen, aryl, heteroaryl, or —S$R_h$; and $R_4$ is a protecting group, and removing the protecting group $R_4$ to provide the compound of formula (I) wherein $R_3$ is hydrogen, aryl, heteroaryl, or —S$R_h$, and $R_4$ is hydrogen. In one embodiment, the catalyst comprises palladium (e.g. $Pd_2$(dba)$_2$). In another embodiment $R_a$ is methyl, ethyl, propyl, or butyl.

The invention also provides a method of preparing a compound of formula (I) wherein $R_3$ is aryl, heteroaryl, or —CH=CHC(=O)N$R_mR_p$, and $R_4$ is hydrogen; comprising: combining a corresponding compound of formula (I) wherein $R_3$ is —Sn(R)$_3$, each R is ($C_1$–$C_6$)alkyl, and $R_4$ is a protecting group, with the requsite organohalide or organotriflate (e.g. a compound of formula $R_3$—X wherein X is a halogen ot triflate) and a catalyst, to provide a compound of formula (I) wherein $R_3$ is aryl, heteroaryl, or —CH=CHC(=O)N$R_mR_p$; and $R_4$ is a protecting group, and removing the protecting group $R_4$ to provide the compound of formula (I) wherein $R_3$ is aryl, heteroaryl, or —CH=CHC(=O)N$R_mR_p$, and $R_4$ is hydrogen. In one embodiment, each R is methyl, ethyl, propyl, or butyl.

The invention also provides a method of preparing a compound of formula (I) wherein $R_3$ is H or F, and $R_4$ is hydrogen; comprising: combining a corresponding compound of formula (I) wherein $R_3$ is —Sn(R)$_3$, each R is ($C_1$–$C_6$)alkyl, and $R_4$ is a protecting group, with AgOTf and $XeF_2$ to provide a compound of formula (I) wherein $R_3$ is H or F; and $R_4$ is a protecting group, and removing the protecting group $R_4$ to provide the compound of formula (I) wherein $R_3$ is is H or F, and $R_4$ is hydrogen. In one embodiment, each R is methyl, ethyl, propyl, or butyl.

Many of the starting materials employed in the synthetic methods described above are commercially available or are reported in the scientific literature. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) can be formulated as pharmaceutical compositions and administered to a mammalian host, such as a human patient in a variety of forms adapted to a selected route of administration, i.e., by oral, parenteral, intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

For veterinary medicine, the composition may, for example, be formulated as an intramammary preparation in either long acting or quick-release bases.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in powder will be about 0.1–5 wt-%, preferably about 0.5–2.5 wt-%.

The compositions per unit dosage, whether liquid or solid may contain from 0.1% to 99% of active material (the present 7-vinylidene cephalosporins and optional antibiotic), the preferred range being from about 10–60%. The composition will generally contain from about 15 mg to about 1500 mg by weight of active ingredient based upon the total weight of the composition; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution. Single dosages for injection, infusion or ingestion may be administered, i.e., 1–3 times daily, to yield levels of about 0.5–50 mg/kg, for adults.

The invention provides a pharmaceutical composition, comprising an effective amount of a compound of formula (I) as described hereinabove; or a pharmaceutically acceptable salt thereof; and a pharmaceutically acceptable carrier. The invention also provides a pharmaceutical composition comprising an effective amount of a compound of formula (I) as described hereinabove; or a pharmaceutically acceptable salt thereof; a β-lactam antibiotic; and a pharmaceutically acceptable carrier. The present compositions are preferably presented in a form suitable for absorption by the gastro-intestinal tract.

Any β-lactam antibiotic is suitable for use in the pharmaceutical composition of the invention. β-lactam antibiotics which are well known in the art include those disclosed by R. B. Morin and M. Gorin, M. Eds.; Academic Press, New York, 1982; vol. 1–3. Preferred β-lactam antibiotics, suitable for use in the pharmaceutical composition of the invention, include β-lactam antibiotics which are preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime.

The ability of a compound of the invention to function as β-lactamase inhibitor can be demonstrated using the test described below, or using other tests which are well known in the art. Representative compounds of formula (I) were evaluated as inhibitors of the Class C β-lactamase of *Enterobacter cloacae* P-99, a cephalosporinase, and TEM-1, a Class A penicillinase, by relative $IC_{50}$ analysis. The $IC_{50}$ value represents the concentration of inhibitor required to effect a 50% loss of activity of free enzyme. The $IC_{50}$ value of each compound was determined as follows. Following a 10 minute incubation of a dilute solution of enzyme (2.56 nM) and inhibitor (<0.64 mM), a 50 mL aliquot of this incubation mixture was then further diluted into 1 mL nitrocefin solution, and the rate of hydrolysis was measured during a 1 minute period by monitoring the absorbance of nitrocefin as a function of time. In addition, the $IC_{50}$ values of tazobactam were determined as relative controls. The data is presented in Table 1 below for representative compounds of the formulae I.

TABLE 1 beta-Lactamase inhibitory activity against representative class A (TEM-1) and class C (P99) enzymes

| Compound | TEM-1 ($IC_{50}$, μm) | P99 ($IC_{50}$, μm) |
| --- | --- | --- |
| 7a | 1.82 | 0.003 |
| 7b | 0.791 | 0.0029 |
| 7c | 1.28 | 0.0047 |
| 9a | 1.065 | 0.059 |
| 9b | 0.012 | 0.0217 |
| 9c | 3.54 | 0.043 |
| 9d | 9.14 | 0.038 |
| 11a | 0.0076 | 0.0907 |
| 11b | 0.0094 | 0.174 |
| 14a | 1.84 | 0.011 |
| 14b | 18.52 | 0.116 |
| 18a | 0.240 | 0.824 |
| 18b | 7.69 | 0.128 |
| 21a | 0.39 | 1.1 |
| 21b | 1.59 | 4.2 |
| 21c | 0.053 | 6.34 |
| tazobactam | 0.25 | 101.6 |

The present β-lactamase inhibitors of formula (I) are particularly useful in the treatment of infections associated with Enterobacter, Citrobacter, and Serratia. These bacteria have the ability to attach to the epithelial cells of the bladder or kidney (causing urinary tract infections) and are resistant to multiple antibiotics including amoxicillin and ampicillin.

The present β-lactamase inhibitors of formula (I) are also be useful in the treatment of infections associated with highly resistant *Pneumococci*. Such diseases include otitis media, sinusitis, meningitis (both in children and adults), bacteremia, and septic arthritis. Resistant pneumococcal strains have surfaced in many parts of the world. For example, in Hungary, 58% of *S. pneumoniae* are resistant to penicillin, and 70% of children who are colonized with *S. pneumoniae* carry resistant strains that are also resistant to tetracycline, erythromycin, trimethoprin/sulfamethoxazole (TMP/SMX), and 30% resistant to chloramphenicol. *Klebsiella pneumoniae* (resistant via the production of β-lactamase) have caused hospital outbreaks of wound infection and septicemia.

Other features of the invention will become apparent in the course of the following descriptions of exemplary embodiments which are given for illustration of the invention and are not intended to be limiting thereof.

EXAMPLES 1–3 (FIG. 1)

Preparation of Compound 2

Diphenylmethyl 7-phenylacetamido-3-(trifluorosulfonyloxy)-3-cephem-4-carboxylate (2). This compound and the subsequent halides were prepared according to the method of Farina (Farina et. al. J. Org. Chem. 54, 4962–4966 (1989)). A solution of benzhydryl 3-hydroxy-7-(phenylacetamido)ceph-3-em (1, 41 g, 84 mmol, commercially available from Otsuka Chemical Corp.) in anhydrous $CH_2Cl_2$ (600 mL) was cooled to −78° C. and treated with dry diisopropylethylamine (15.6 mL, 90 mmol) and trifluoromethanesulfonic anhydride (14.3 mL, 85 mmol). The mixture was then stirred at −78° C. for 20 min. The solution was then diluted with an addition 1 L of dry $CH_2Cl_2$ and the cooling bath was removed. The organic phase was washed with water (2×1 L) and brine (1×500 mL). Then it was dried over $Na_2SO_4$ and concentrated to afford the desired triflate (2) as an off-white amorphous powder. Yield=43.5 g (85%).
$^1$H NMR ($CDCl_3$, 400 MHz) δ=3.42 (d, J=18 Hz, 1H), 3.70–3.63 (m, 2H), 3.75 (d, J=18 Hz, 1H), 5.03 (d, J=5 Hz, 1H), 5.91–5.87 (m, 1H), 6.02 (d, J=8.7 Hz, 1H), 6.98 (s, 1H), 7.51–7.24 (m, 15H).

Preparation of Compounds 3a–3c

General Procedure for the Synthesis of Diphenylmethyl 3-halo-7-(phenylacetamido)-3-cephem-4-carboxylates (3a, 3b, and 3c).

To a solution of triflate 2 (10 mmol) in anhydrous THF (100 mL) was added fresh anhydrous LiX (25 mmol) and the reaction was allowed to stir under argon for 24 to 36 h while monitoring the progress by $^1$H NMR. When the reaction was complete, water (200 mL) and EtOAc (200 mL) were added and the organic phase was washed with water (2×100 mL), followed by brine (1×100 mL) and dried over $Na_2SO_4$. Evaporation of the solvent produced the crude 3-halo-3-cephem-4-carboxylate ester which was further purified by column chromatography on silica gel.

Diphenylmethyl 3-chloro-7-(phenylacetamido)-3-cephem-4-carboxylate (3a).

Yield=90%. $^1$H NMR ($CDCl_3$, 400 MHz) δ=3.43 (d, J=18.5 Hz, 1H), 3.64–3.57 (m, 2H), 3.74 (d, J=18.5 Hz, 1H), 4.99 (d, J=5 Hz, 1H), 5.84–5.81 (m, 1H), 6.24 (d, J=9 Hz, 1H), 6.97 (s, 1H), 7.39–7.24 (m, 15H).

Diphenylmethyl 3-bromo-7-(phenylacetamido)-3-cephem-4-carboxylate (3b).

Yield=88%. $^1$H NMR ($CDCl_3$, 400 MHz) δ=3.64–3.56 (m, 3H), 3.83 (d, J=18 Hz, 1H), 5.02 (d, J=5 Hz, 1H), 5.81–5.78 (m, 1H), 6.21 (d, J=9 Hz, 1H), 6.97 (s, 1H), 7.41–7.25 (m, 15H).

Diphenylmethyl 3-iodo-7-(phenylacetamido)-3-cephem-4-carboxylate (3c).

Yield=72%. $^1$H NMR ($CDCl_3$, 400 MHz) δ=3.67–3.56 (m, 2H), 3.70 (d, J=18.5 Hz, 1H), 3.84 (d, J=18.5 Hz, 1H), 5.04 (d, J=5 Hz, 1H), 5.85–5.81 (m, 1H), 6.16 (d, J=9 Hz, 1H), 6.96 (s, 1H), 7.41–7.24 (m, 15H).

Preparation of Compounds 4a–4c

General Procedure for the Synthesis of Diphenylmethyl 3-halo-7-amino-3-cephem-4-carboxylates (4a, 4b, and 4c).

To a cooled (0° C.) solution of $PCl_5$ (25 mmol) in dry $CH_2Cl_2$ was added dry pyridine (25 mmol) slowly while cooling the reaction with an ice bath. The reaction was allowed to stir at this temperature for 1 h. The appropriate phenylacetamido-3-cephem-4-carboxylate (3a, 3b, or 3c) was then added in one portion and the reaction allowed to continue stirring for 1.5 h at the same temperature. The reaction mixture was then cooled to −78° C. and MeOH (30 mL) was added slowly and the reaction stirred for an additional 1 h. The reaction mixture was then allowed to slowly warm to reach a temperature between −10 and 0° C. Water (30 mL) was then added and the solution was concentrated under vacuum to remove $CH_2Cl_2$ and most of the MeOH. To the remaining residue, EtOAc (150 mL) and water (100 mL) were added and the water layer was basified by the addition of $NaHCO_3$. The organic layer was then separated and the aqueous layer was further extracted with EtOAc (1×50 mL). The combined organic layer was washed with water (1×100 mL) followed by brine (1×100 mL). The organic layer was then dried over $Na_2SO_4$ and concentrated under vacuum. The crude product was further purified by column chromatography using a mixture of EtOAc and $CH_2Cl_2$ as eluent.

Diphenylmethyl 3-chloro-7-amino-3-cephem-4-carboxylate (4a).

Yield=74%. $^1$H NMR ($CDCl_3$, 400 MHz) δ=1.74 (br s, 2H), 3.48 (d, J=18.5 Hz, 1H), 3.8 (d, J=18.5 Hz, 1H), 4.75 (d, J=5.0 Hz, 1H), 4.98 (d, J=5.0 Hz, 1H), 7.00 (s, 1H), 7.57–7.26 (m, 10H).

Diphenylmethyl 3-bromo-7-amino-3-cephem-4-carboxylate (4b).

Yield=72%. $^1$H NMR ($CDCl_3$, 400 MHz) δ=1.74 (br s, 2H), 3.62 (d, J=18 Hz, 1H), 3.88 (d, J=18 Hz, 1H), 4.75 (d, J=5.0 Hz, 1H), 5.00 (d, J=5.0 Hz, 1H), 7.00 (s, 1H), 7.44–7.25 (m, 10H).

Diphenylmethyl 3-iodo-7-amino-3-cephem-4-carboxylate (4c).

Yield=76%. $^1$H NMR ($CDCl_3$, 400 MHz) δ=1.75 (br s, 2H), 3.76 (d, J=18.5 Hz, 1H), 3.90 (d, J=18.5 Hz, 1H), 4.75 (d, J=5 Hz, 1H), 5.04 (d, J=5.0 Hz, 1H), 7.00 (s, 1H), 7.46–7.26 (m, 10H).

Preparation of Compounds 5a–5c

General Procedure for Synthesis of Diphenylmethyl 3-halo-7-(2'-pyridylmethylidene)-3-cephem-4-carboxylates (4a, 4b, and 4c)

To a solution of triphenyl(2-pyridylmethyl)phosphonium chloride hydrochloride (20 mmol, Aldrich Chemical Co.) in anhydrous THF (150 mL) was added potassium tert-butoxide (15 mmol). This slurry was then s the Wittig Reagent.

Separately, to a solution of amine (4, 20 mmol) in EtOAc (200 mL) were added catalytic trifluoroacetic acid (200 μL) and isopropylnitrite (a solution 30 to 50% in $CH_2Cl_2$, prepared by the method of Blacklock et. al., J. Org. Chem., 54, 3907–3913 (1989)). After completion of the reaction (approx. 5 min, monitored by TLC), EtOAc was removed under vacuum and the resultant 7-diazo-3-cephem-4-carboxylates was dried completely under high vacuum. This diazo compound was then immediately dissolved in anhydrous benzene (200 mL) and propylene oxide (25 mL), and treated with a catalytic amount of rhodium octanoate (0.5 g). The reaction was observed to evolve gas. After the completion of such gas evolution, the benzene solvent was removed under vacuum and the remaining solid (7-oxo-3-cephem-4-carboxylate) dissolved in dry $CH_2Cl_2$ (200 mL). This solution was then cooled to −78° C.

The solution of the aforementioned Wittig Reagent was then slowly added (via cannula) to this cold (−78° C.) solution of ketone and the reaction stirred at this temperature for 30 min. Then a saturated aqueous solution of $NH_4Cl$ was added and the reaction mixture slowly warmed to room temperature with stirring. The layers were separated and the aqueous layer extracted with an additional portion of $CH_2Cl_2$. The combined organic layers were washed with water (1×100 mL), brine (1×100 mL), and dried over $Na_2SO_4$. The crude product was purified by column chromatography (silica gel) using a mixture of EtOAc and $CH_2Cl_2$ as eluent.

Diphenylmethyl 3-chloro-7-(2'-pyridylmethylidene)-3-cephem-4-carboxylate (5a).

Overall yield (three steps from 4a)=35%. $^1$H NMR (CDCl$_3$, 400 MHz) δ=3.54 (d, J=18.5 Hz, 1H), 3.96 (d, J=18.5 Hz, 1H), 5.71 (s, 1H), 7.03 (s, 1H), 7.41–7.28 (m, 13H), 7.76 (t of d, J=1.6 Hz and 7.7 Hz, 1H), 8.76 (d, J=4Hz, 1H).

Diphenylmethyl 3-bromo-7-(2'-pyridylmethylidene)-3-cephem-4-carboxylate (5b).

Overall yield (three steps from 4b)=35%. $^1$H NMR (CDCl$_3$, 400 MHz) δ=3.59 (d, J=18.5 Hz, 1H), 3.95 (d, J=18.5 Hz, 1H), 5.73 (d, J=1 Hz, 1H), 7.05 (s, 1H), 7.47–7.26 (m, 13H), 7.77 (t of d, J=1.6 Hz and 7.7 Hz, 1H), 8.76 (d, J=4 Hz, 1H).

Diphenylmethyl 3-iodo-7-(2'-pyridylmethylidene)-3-cephem-4-carboxylate (5c).

Overall yield (three steps from 4a)=33%. $^1$H NMR (CDCl$_3$, 400 MHz) δ=3.70 (d, J=18.5 Hz, 1H), 3.94 (d, J=18.5 Hz, 1H), 5.76 (s, 1H), 7.06 (s, 1H), 7.42–7.26 (m, 13H), 7.73 (t of d, J=1.6 and 7.7 Hz, 1H), 8.71 (d, J=4.0 Hz, 1H).

Preparation of Compounds 6a–6c

General Procedure for Formation of Diphenylmethyl 1,1-dioxo-3-halo-7-(2'-pyridylmethylidene)-3-cephem-4-carboxylates (6a, 6b, and 6c) Using Oxidation with mCPBA.

To a solution of sulfide (5) in CH$_2$Cl$_2$ (15 mL) was added mCPBA (2.5 mmol) and the reaction was stirred for 20 min at rt. A saturated aqueous solution of Na$_2$SO$_3$ was then added and the layers were separated. The organic layer was washed with aqueous NaHCO$_3$ (1×25 mL), water (1×25 mL), and brine (1×25 mL). The organic layer was then dried over Na$_2$SO$_4$, concentrated and the crude product further purified by flash column chromatography (silica gel) using a mixture of EtOAc and CH$_2$Cl$_2$ as eluent.

Diphenylmethyl 3-chloro-1,1-dioxo-7-(2'-pyridylmethylidene)-3-cephem-4-carboxylate (6a).

Yield=72%. $^1$H NMR (CDCl$_3$, 400 MHz) δ=4.04 (d, J=18 Hz, 1H), 4.23 (d, J=18 Hz, 1H), 5.93 (s, 1H), 7.03 (s, 1H), 7.39–7.31 (m, 13H), 7.73 (t of d, J=1.6 Hz and 7.7 Hz, 1H), 8.66 (d, J=4 Hz, 1H).

Diphenylmethyl 3-bromo-1,1-dioxo-7-(2'-pyridylmethylidene)-3-cephem-4-carboxylate (6b).

Yield=75%. $^1$H NMR (CDCl$_3$, 400 MHz) δ=4.10 (d, J=18 Hz, 1H), 4.34 (d of t, J=18 Hz, 1H), 5.95 (s, 1H), 7.04 (s, 1H), 7.47–7.3 (m, 13H), 7.73 (t of d, J=1.6 Hz and 7.7 Hz, 1H), 8.67 (d, J=4 Hz, 1H).

Diphenylmethyl 3-iodo-1,1-dioxo-7-(2'-pyridylmethylidene)-3-cephem-4-carboxylate (6c).

Yield=78%. $^1$H NMR (CDCl$_3$, 400 MHz) δ=8.66 (d, J=4.0 Hz, 1H), 7.71 (t of d, J=1.6 and 7.7 Hz, 1H), 7.49–7.25 (m, 13H), 7.03 (s, 1H), 5.96 (s, 1H), 4.38 (d, J=18 Hz, 1H), 4.18 (d, J=18 Hz, 1H). $^{13}$C NMR (CDCl$_3$, 400 MHz) δ=160.3, 160.2, 150.4, 150.2, 138.9, 138.6, 137.0, 132.7, 130.9, 128.6, 128.5, 128.4, 128.2, 128.0, 127.5, 127.2, 126.6, 126.4, 125.3, 80.5, 74.1, 64.2. HRMS calcd for C$_{26}$H$_{19}$IN$_2$O$_5$S [M+H]$^+$ 599.0138, obsd 599.0135.

Preparation of Compounds 7a–7c

General Procedure for the Deprotection of Benzhydryl Esters.

A solution of the appropriate benzhydryl ester (0.1 mmol) in dry anisole (3.0 mmol) was cooled in an ice-salt bath and trifluoroacetic acid (12.0 mmol) was added slowly via syringe under argon atmosphere. After 20 minutes, the volatile components were removed under vacuum and the residue was dissolved in EtOAc (5 mL). The EtOAc layer was extracted with aqueous NaHCO$_3$ (2×0.15 mmol in 4 mL H$_2$O). The combined water layers were directly loaded onto a chromatography column (high porous polymer, MCI gel, CHP20P Mitsubishi Chemical Corp., White Plains N.Y., approx. 75 to 150 mL of resin) and the product eluted with 5% EtOH in deionized water. The yield was typically between 60 to 80%.

EXAMPLE 1

Sodium 3-chloro-1,1-dioxo-7-(2'-pyridylmethylidine)-3-cephem-4-carboxylate (7a).

Prepared from ester 7a according to the general procedure described above for the deprotection of benzhydryl esters. $^1$H NMR (D$_2$O, 400 MHz) δ=6.28 (s, 1H), 7.44–7.34 (m, 1H), 7.48 (s, 1H), 7.62–7.59 (m, 1H), 7.84 (t of d, J=1.6 Hz and 7.7 Hz, 1H), 8.55 (d, J=4.0 Hz, 1H).

EXAMPLE 2

Sodium 3-bromo-1,1-dioxo-7-(2'-pyridylmethylidine)-3-cephem-4-carboxylate (7b).

Prepared from ester 7b according to the general procedure described above for the deprotection of benzhydryl esters. $^1$H NMR (D$_2$O, 400 MHz) δ=6.29 (s, 1H), 7.45–7.35 (m, 1H), 7.49 (s, 1H), 7.6–7.57 (m, 1H), 7.85 (t of d, J=1.6 and 7.7 Hz, 1H), 8.56 (d, J=4.0 Hz, 1H).

EXAMPLE 3

Sodium 1,1-dioxo-3-iodo-7-(2'-pyridylmethylidine)-3-cephem-4-carboxylate (7c).

Prepared from ester 7c according to the general procedure described above for the deprotection of benzhydryl esters. $^1$H NMR (D$_2$O, 400 MHz) δ=6.29 (d, J=1Hz, 1H), 7.33–7.30 (m, 1H), 7.45 (d, J=1Hz, 1H), 7.65–7.61 (m, 1H), 7.83 (t of d, J=1.6 Hz and 7.7 Hz, 1H), 8.54 (d, J=4.0Hz, 1H).

EXAMPLES 4–7 (FIG. 2)

Preparation of Compounds 8–8d

General Procedure for the Stille Couplings of Iodide 6c with Organostannanes to Produce Compounds 8a–8d To a solution of 6c (72 mg, 0.12 mmol) in anhydrous THF were added the appropriate organostannane (0.11 mmol, e.g., Bu$_3$Sn—R$_3$) and Pd$_2$(dba)$_3$ (5 mg, 0.011 mmol) under an Ar atmosphere. The reaction mixture was stirred at 65° C. for 2.5 h and was monitored by $^1$H NMR. After completion of the reaction, solvent was removed under reduced pressure and the product dissolved in CH$_2$Cl$_2$. The solution was then washed with water (10 mL) and brine (10 mL). The organic layer was concentrated and purified by column chromatography (silica gel).

Diphenylmethyl 1,1-dioxo-3-methylsulfanyl-7-(2'-pyridylmethylidine)-3-cephem-4-carboxylate (8a).

Yield=67%. $^1$H NMR (CDCl$_3$, 400 MHz) δ=2.35 (s, 3H), 3.98 (d, J=15.5 Hz, 1H), 4.18 (d, J=15.5 Hz, 1H), 5.72 (d, J=1 Hz, 1H), 6.97 (s, 1H), 7.4–7.26 (m, 13H), 7.71 (t of d, J=1.6 and 7.7 Hz, 1H), 8.66 (d, J=4 Hz, 1H).

Diphenylmethyl 1,1-dioxo-3-phenylsulfanyl-7-(2'-pyridylmethylidine)-3-cephem-4-carboxylate (8b).

Yield=72%. $^1$H NMR (CDCl$_3$, 400 MHz) δ=8.63 (d, J=3.9 Hz, 1H), 7.71 (t of d, J=1.6 and 7.7 Hz, 1H), 7.53–7.26 (m, 19H), 7.02 (s, 1H), 5.75 (s, 1H), 3.75 (d, J=15.6 Hz, 1H), 3.59 (d, J=15.6 Hz, 1H).

Diphenylmethyl 1,1-dioxo-7-(2'-pyridylmethylidine)-3-(thiophen-2'-yl)-3-cephem-4-carboxylate (8c).

Yield=78%. $^1$H NMR (CDCl$_3$, 400 MHz) δ=8.69 (d, J=4.0 Hz, 1H), 7.72 (t of d, J=1.6 and 7.7 Hz, 1H), 7.4–7.21

(m, 12H), 7.07–7.05 (m, 2H), 6.96 (s, 1H), 6.84 (dd, J=1 and 4 Hz, 1H), 6.75 (t, J=4 Hz, 1H), 5.96 (s, 1H), 4.17 (d, J=18 Hz, 1H), 4.08 (d, J=18 Hz, 1H).

Diphenylmethyl 1,1-dioxo-3-phenyl-7-(2'-pyridylmethylidine)-3-cephem-4-carboxylate (8d).

Yield=56%. $^1$H NMR (CDCl$_3$, 400 MHz) δ=8.65 (d, J=3.9 Hz, 1H), 7.7 (t of d, J=1.6 and 7.7 Hz, 1H), 7.34–7.13 (m, 16H), 6.92 (d, J=6.7 Hz, 2H), 6.85 (s, 1H), 5.98 (s, 1H), 4.08 (s, 2H). $^{13}$C NMR (CDCl$_3$, 400 MHz) δ=160.8, 159.2, 150.2, 150.0, 138.6, 138.1, 136.5, 134.9, 132.8, 129.9, 128.9, 128.5, 128.09, 127.9, 127.7, 127.5, 127.2, 127.0, 126.9, 125.9, 124.7, 79.0, 73.0, 56.7.

Preparation of Compounds 9a–9d

Compounds 9a–9d were prepared from Compounds 8a–8d Using the General Procedure for the Deprotection of benzhydryl esters described above.

EXAMPLE 4

Sodium 1,1-dioxo-3-methylsulfanyl-7-(2'-pyridylmethylidine)-3-cephem-4-carboxylate (9a).

Prepared from ester 8a according to the general procedure described above for the deprotection of benzhydryl esters. $^1$H NMR (D$_2$O, 400 MHz) δ=2.2 (s, 3H), 6.17 (s, 1H), 7.42-7.36 (m, 2H), 7.43 (s, 1H), 7.61–7.58 (m, 1H), 7.81 (t of d, J=1.6 Hz and 7.7 Hz, 1H), 8.52 (d, J=4.0 Hz, 1H).

EXAMPLE 5

Sodium 1,1-dioxo-3-phenylsulfanyl-7-(2'-pyridylmethylidine)-3-cephem-4-carboxylate (9b).

Prepared from ester 8b according to the general procedure described above for the deprotection of benzhydryl esters. $^1$H NMR (D$_2$O, 400 MHz) δ=6.32 (d, J=1 Hz, 1H), 7.42–7.33 (m, 6H), 7.46 (s, 1H), 7.6–7.58 (m, 1H), 7.81 (t of d, J=1.6 Hz and 7.7 Hz, 1H), 8.51 (d, J=4.0 Hz, 1H).

EXAMPLE 6

Sodium 1,1 -dioxo-7-(2'-pyridylmethylidine)-3-(thiophen-2'-yl)-3-cephem-4-carboxylate (9c).

Prepared from ester 8c according to the general procedure described above for the deprotection of benzhydryl esters. $^1$H NMR (D$_2$O, 400 MHz) δ=6.23 (s, 1H), 7.03–7.00 (m, 1H), 7.1 (d, J=4 Hz, 1H), 7.42–7.4 (m, 2H), 7.45 (s, 1H), 7.61 (d, J=7.6 Hz, 1H), 7.83 (t of d, J=1.6 Hz and 7.7 Hz, 1H), 8.54 (d, J=4.0 Hz, 1H).

EXAMPLE 7

Sodium 1,1-dioxo-3-phenyl-7-(2'-pyridylmethylidine)-3-cephem-4-carboxylate (9d).

Prepared from ester 8d according to the general procedure described above for the deprotection of benzhydryl esters. $^1$H NMR (D$_2$O, 400 MHz) δ6.24 (s, 1H), 7.39–7.28 (m, 6H), 7.45 (s, 1H), 7.62–7.60 (m, 1H), 7.82 (t of d, J=1.6 Hz and 7.6 Hz, 1H), 8.54 (d, J=4.0 Hz, 1H).

EXAMPLES 8 AND 9 (FIG. 3)

Preparation of Compounds 10a and 10b

General Procedure for Oxidation of the 3-Position Sulfur of Compounds 8a and 8b to Produce the Corresponding 3-Position Surfones (10a and 10b).

To a solution of sulfide (8a or 8b, 0.1 mmol) in CH$_2$Cl$_2$ (5 mL) was added mCPBA (0.4 mmol) and the reaction mixture stirred at room temperature until the reaction was complete (monitored by TLC, approx. 8 h). The reaction was then quenched by the addition of a saturated solution of NaHSO$_3$. The layers were separated and the aqueous layer extracted with an addition portion of CH$_2$Cl$_2$ (1×20 mL). The combined organic layers were washed with NaHCO$_3$ (1×20 mL), water (1×20 mL), and brine (1×20 mL). The organic layer was then dried over Na$_2$SO$_4$, concentrated under vacuum, and purified by flash chromatography (silica gel).

Diphenylmethyl 1,1-dioxo-3-methylsulfonyl-7-(2'-pyridylmethylidine)-3-cephem-4-carboxylate (10a).

Yield=81%. $^1$H NMR (CDCl$_3$, 400 MHz) δ=2.81 (s, 3H), 3.84 (d, J=18.5 Hz, 1H), 4.34 (d, J=18.5 Hz, 1H), 6.08 (s, 1H), 7.03 (s, 1H), 7.43–7.3 (m, 13H), 7.74 (t of d, J=1.6 Hz and 7.7 Hz, 1H), 8.69 (d, J=4 Hz, 1H).

Diphenylmethyl 1,1-dioxo-3-phenylsulfonyl-7-(2'-pyridylmethylidine)-3-cephem-4-carboxylate (10b).

Yield=75%. $^1$H NMR (CDCl$_3$, 400 MHz) δ=3.48 (d, J=18 Hz, 1H), 4.16 (d, J=18 Hz, 1H), 5.94 (s, 1H), 7.05 (s, 1H), 7.44–7.19 (m, 17H), 7.75–7.71 (m, 2H), 8.61 (d, J=4 Hz, 1H).

Preparation of Compounds 11a and 11b

Compounds 11a and 11b were prepared from Compounds 10a and 10b using the General Procedure for the Deprotection of benzhydryl esters described above.

EXAMPLE 8

Sodium 1,1-dioxo-3-methylsulfonyl-7-(2'-pyridylmethylidine)-3-cephem-4-carboxylate (11a).

Prepared from ester 10a according to the general procedure described above for the deprotection of benzhydryl esters. $^1$H NMR (D$_2$O, 400 MHz) δ=3.2 (s, 3H), 4.53 (d, J=17.6 Hz, 1H), 4.32 (d, J=17.6 Hz, 1H), 6.41 (s, 1H), 7.49–7.40 (m, 1H), 7.66–7.58 (m, 2H), 7.86 (t of d, J=1.6 and 7.6 Hz, 1H), 8.60 (d, J=4.0 Hz, 1H).

EXAMPLE 9

Sodium 1,1 -dioxo-3-phenylsulfonyl-7-(2'-pyridylmethylidine)-3-cephem-4-carboxylate (11b).

Prepared from ester 10b according to the general procedure described above for the deprotection of benzhydryl esters. $^1$H NMR (D$_2$O, 400 MHz) δ=6.33 (s, 1H), 7.40–7.39 (m, 1H), 7.62–7.54 (m, 6H), 7.71 (m, 1H), 7.83 (t of d, J=1.6 and 7.6 Hz, 1H), 8.55 (d, J=4.0 Hz, 1H).

EXAMPLES 10 AND 11 (FIG. 4)

Preparation of Compounds 12

Diphenylmethyl 1,1 -dioxo-7-(2'-pyridylmethylidine)-3-(trimethylstannyl)-3-cephem-4-carboxylate (12).

To a solution of 6c (1.0 g, 1.71 mmol) in dry THF was added hexamethylditin (0.67 g, 2.0 mmol), Pd$_2$(dba)$_3$ (175 mg, 0.2 mmol) under an Ar atmosphere. The reaction mixture was stirred at 60° C. for 1.5 h, while monitoring by $^1$H NMR. After completion of the reaction, solvent was removed under reduced pressure. The product was then dissolved in CH$_2$Cl$_2$ and washed with water (50 mL) and brine (30 mL). The organic layer was dried (Na$_2$SO$_4$), concentrated under reduced pressure, and purified by flash chromatography using EtOAc/CH$_2$Cl$_2$ as eluent to obtain a 60% yield of 13. $^1$H NMR (CDCl$_3$, 400 MHz): δ=8.66 (d, J=3.9 Hz, 1H), 7.72 (t of d, J=1.6 and 7.7 Hz, 1H), 7.54 (d, J=7.5 Hz, 2H), 7.43 to 7.26 (m, 11H), 6.92 (s, 1H), 5.88 (s, 1H), 4.07 (d, J=18.5 Hz, 1H), 3.93 (d, J=18.5 Hz, 1H), 0.15 (s, 9H). $^{13}$C NMR (CDCl$_3$, 400 MHz) δ=162.6, 158.4, 150.8, 150.3, 142.1, 139.6, 139.2, 136.8, 133.9, 130.6, 129.8, 128.6, 128.4, 128.2, 127.9, 127.5, 127.1, 126.0, 124.9, 80.3, 73.1, 57.6, −6.6. HRMS calcd for C$_{29}$H$_{29}$N$_2$O$_5$SSn [M+H]$^+$ 637.0819, obsd 637.0823.

Preparation of Compounds 13a and 13b

Reaction of 12 with XeF$_2$: Synthesis of diphenylmethyl 1,1-dioxo-3-fluoro-7-(2'-pyridylmethylidine)-3-cephem-4-carboxylate (13a) and diphenylmethyl 1,1-dioxo-7-(2'-pyridylmethylidine)-3-cephem-4-carboxylate (13b).

To a solution of stannane 12 (0.1 mmol) in anhydrous CH$_2$Cl$_2$ was added AgOTf (0.11 mmol) and the reaction mixture was cooled in an ice-salt bath under argon. XeF$_2$ (0.11 mmol) was then added in one portion and the reaction stirred for 10 min. At this time, water was added, the layers separated. The aqueous layer was extracted with an additional portion of CH$_2$Cl$_2$ (1×25 mL), and the combined organic layers were washed with water (1×25 mL) and brine (1×25 mL) and dried over Na$_2$SO$_4$. After the solvent was removed under vacuum, the products were purified by flash chromatography on silica gel.

Diphenylmethyl 1,1-dioxo-3-fluoro-7-(2'-pyridylmethylidine)-3-cephem-4-carboxylate (13a).

$^1$H NMR (CDCl$_3$, 400 MHz) δ=8.65 (d, J=4.0 Hz, 1H), 7.71 (t of d, J=1.5 and 7.7 Hz, 1H), 7.47–7.27 (m, 13H), 7.04 (s, 1H), 5.84 (s, 1H), 4.23 (d of d, J=5.4 and 20 Hz, 1H), 4.08 (d of d, J=5.4 and 20 Hz, 1H).

Diphenylmethyl 1,1-dioxo-7-(2'-pyridylmethylidine)-3-cephem-4-carboxylate (13b).

$^1$H NMR (CDCl$_3$, 400 MHz) δ=8.66 (d, J=4.0 Hz, 1H), 7.76 (t of d, J=1.5 and 7.7 Hz, 1H), 7.48–7.25 (m, 13H), 6.99 (s, 1H), 6.34 (d of d, J=3.5 and 2.0 Hz), 5.94 (s, 1H), 4.04 (d of d, 1.5 and 17.5 Hz, 1H), 3.83 (d of d, J=5.6 and 17.5 Hz, 1H). HRMS calcd for C$_{26}$H$_{21}$N$_2$O$_5$S [M+H]$^+$ 473.1171, obsd 473.1148.

Preparation of Compounds 14a and 14b

Compounds 14a and 14b were prepared from Compounds 13a and 13b using the General Procedure for the Deprotection of benzhydryl esters described above.

EXAMPLE 10

Sodium 1,1-dioxo-3-fluoro-7-(2'-pyridylmethylidine)-3-cephem-4-carboxylate (14a).

Prepared from ester 13a according to the general procedure described above for the deprotection of benzhydryl esters. $^1$H NMR (D$_2$O, 400 MHz) δ=6.19 (s, 1H), 7.46–7.35 (m, 2H), 7.58–7.55 (m, 1H), 7.8 (t of d, J=1.6 Hz and 7.6 Hz, 1H), 8.52 (d, J=4.0 Hz, 1H).

EXAMPLE 11

Sodium 1,1-dioxo-7-(2'-pyridylmethylidine)-3-cephem-4-carboxylate (14b).

Prepared from ester 13b according to the general procedure described above for the deprotection of benzhydryl esters. $^1$H NMR (D$_2$O, 400 MHz) δ=6.21 (s, 1H), 7.38–7.35 (m, 1H), 7.43 (s, 1H), 7.61–7.59 (m, 1H), 7.81 (t of d, J=1.6 Hz and 7.6 Hz, 1H), 8.51 (d, J=4.0 Hz, 1H).

EXAMPLES 12–16 (FIGS. 5 AND 6)

Preparation of Compounds 16a, 16b, and 20a–20c

General procedure for the formation of amides from carboxylic acids (Schemes 5 and 6). The following procedure was used to prepare compound 16a and 16b from compound 15 and was also used to prepare compounds 20a, 20b and 20c from compound 19.

To a solution of the carboxylic acid (0.3 mmol) in dry CH$_3$CN (10 mL) was added Et3N (0.6 mmol), the appropriate amine, RNH$_2$ (0.45 mmol), and BOP reagent (0.3 mmol) at room temperature. The reaction was monitored by TLC and was usually complete in 30 min. CH$_3$CN was then removed under vacuum. To the residue was added CH$_2$Cl$_2$ (25 mL) and water (25 mL). After separation of the layers, the aqueous layer was extracted a second time with CH$_2$Cl$_2$ (25 mL) and the combined organic layers were washed with water (10 mL) followed by brine (25 mL). These organic layers were then dried over Na$_2$SO$_4$, concentrated under vacuum, and purified by column chromatography. The yields of these coupling reactions were typically 50 to 70%.

Preparation of Compounds 17a, 17b, and 19

General procedure used for the oxidation of sulfides 16a and 16b to the corresponding sulfones 17a and 17b as well as for the oxidation of sulfide 15 to sulfone 19.

This procedure is identical to the general procedure for formation of diphenylmethyl 1,1-dioxo-3-halo-7-(2'-pyridylmethylidene)-3-cephem-4-carboxylates (6a, 6b, and 6c) using oxidation with mCPBA which is described above.

Preparation of Compounds 18a, 18b, and 21a–21c

General Procedure for the Deprotection of the Benzhydryl Esters (17a, 17b, 20a, 20b, and 20c) to Produce the Corresponding Carboxylic Acid Salts (18a, 18b, 21a, 21b, and 21c, Respectively).

This procedure is identical to the General Procedure for the deprotection of benzhydryl esters described above.

EXAMPLE 12

Sodium 3-(N-cyclopropyl-2'-carbamoylvinyl)-1,1-dioxo-7-2"-pyridylmethylidine)-3-cephem-4-carboxylate (18a)

$^1$H NMR (D$_2$O, 400 MHz) δ=0.56–0.52 (m, 2H), 0.8 –0.75 (m, 2H), 2.68–2.65 (m, 1H), 4.26 (d, J=17.5 Hz, 1H), 4.39 (d, J=17.5 Hz, 1H), 5.95 (d, J=15.5 Hz, 1H), 6.38 (s, 1H), 7.5–7.45 (m, 2H), 7.57 (s, 1H), 7.69 (d, J=8 Hz, 1H), 7.9 (t of d, J=1.6 Hz and 7.7 Hz, 1H), 8.63 (d, J=4 Hz, 1H).

EXAMPLE 13

Sodium 3-(N-hydroxy-2'-carbamoylvinyl)-1,1-dioxo-7-(2"-pyridylmethylidine)-3-cephem-4-carboxylate (18b)

$^1$H NMR (D$_2$O, 400 MHz) δ=5.88 (d, J=16 Hz, 1H), 6.33 (s, 1H), 7.33 (d, J=16 Hz, 1H), 7.45–7.41 (m, 1H), 7.49 (s, 1H), 7.65 (d, J=8 Hz, 1H), 7.86 (t of d, J=1.6 Hz and 7.7 Hz, 1H), 8.6 (d, J=4 Hz, 1H).

EXAMPLE 14

Sodium 3-[2'-(hydrazinocarbonyl)vinyl]-1,1-dioxo-7-(2"-pyridylmethylidine)-3-cephem-4-carboxylate (21a)

$^1$H NMR (D$_2$O, 400 MHz) δ=5.92 (d, J=16 Hz, 1H), 6.25 (s, 1H), 7.68–7.43 (m, 3H), 7.67 (d, J=8 Hz, 1H), 7.88 (t of d, J=1.6 Hz and 7.7 Hz, 1H), 8.61 (d, J=4 Hz, 1H).

EXAMPLE 15

Sodium 3-{[N-(3"-aminopropyl)-2'-carbamoyl]vinyl)}-1,1-dioxo-7-(2'''-pyridylmethylidine-3-cephem-4-carboxylate (21b)

$^1$H NMR (D$_2$O, 400 MHz) δ=1.87 (q, J=7 Hz, 2H), 2.96 (t, J=7.5 Hz, 1H), 3.31 (t, J=6.5 Hz, 1H), 5.98 (d, J=16 Hz, 1H), 6.33 (s, 1H), 7.48–7.40 (m, 2H), 7.52 (s, 1H), 7.64 (d, J=8 Hz, 1H), 7.85 (t of d, J=1.6 Hz and 7.7 Hz, 1H), 8.58 (d, J=4 Hz, 1H).

EXAMPLE 16

Sodium 3-[3'-(4"-methylpiperazin-1"-yl)-3'-oxopropenyl]-1,1-dioxo-7-(2'''-puridylmethylidine)-3-cephem-4-carboxylate (21c)

$^1$H NMR (D$_2$O, 400 MHz) δ=2.19 (s, 3H), 2.46–2.42 (m, 4H), 3.8–3.76 (m, 4H), 6.37 (d, J=1.6 Hz, 1H), 6.43 (s, 1H), 7.51–7.4 (m, 3H), 7.53 (s, 1H), 7.66 (d, J=16 Hz, 1H), 7.86 (t of d, J=1.6 Hz and 7.7 Hz, 1H), 8.59 (d, J=4 Hz, 1H).

EXAMPLE 17

The following illustrate representative pharmaceutical dosage forms, containing a compound of Formula (I) ('Compound X'), for therapeutic or prophylactic use in humans.

| (i) | Tablet 1 | mg/tablet |
|---|---|---|
| | 'Compound X' | 100.0 |
| | Lactose | 77.5 |
| | Povidone | 15.0 |
| | Croscarmellose sodium | 12.0 |
| | Microcrystalline cellulose | 92.5 |
| | Magnesium stearate | 3.0 |
| | | 300.0 |

| (ii) | Tablet 2 | mg/tablet |
|---|---|---|
| | 'Compound X' | 20.0 |
| | Microcrystalline cellulose | 410.0 |
| | Starch | 50.0 |
| | Sodium starch glycolate | 15.0 |
| | Magnesium stearate | 5.0 |
| | | 500.0 |

| (iii) | Capsule | mg/capsule |
|---|---|---|
| | 'Compound X' | 10.0 |
| | Colloidal silicon dioxide | 1.5 |
| | Lactose | 465.5 |
| | Pregelatinized starch | 120.0 |
| | Magnesium stearate | 3.0 |
| | | 600.0 |

| (iv) | Injection 1 (1 mg/ml) | mg/ml |
|---|---|---|
| | 'Compound X' (free acid form) | 1.0 |
| | Dibasic sodium phosphate | 12.0 |
| | Monobasic sodium phosphate | 0.7 |
| | Sodium chloride | 4.5 |
| | 1.0 N Sodium hydroxide solution (pH adjustment to 7.0–7.5) | q.s. |
| | Water for injection | q.s. ad 1 mL |

| (v) | Injection 2 (10 mg/ml) | mg/ml |
|---|---|---|
| | 'Compound X' (free acid form) | 10.0 |
| | Monobasic sodium phosphate | 0.3 |
| | Dibasic sodium phosphate | 1.1 |
| | Polyethylene glycol 400 | 200.0 |
| | 01 N Sodium hydroxide solution (pH adjustment to 7.0–7.5) | q.s. |
| | Water for injection | q.s. ad 1 mL |

| (vi) | Aerosol | mg/can |
|---|---|---|
| | 'Compound X' | 20.0 |
| | Oleic acid | 10.0 |
| | Trichloromonofluoromethane | 5,000.0 |
| | Dichlorodifluoromethane | 10,000.0 |
| | Dichlorotetrafluoroethane | 5,000.0 |

| (vii) | Tablet 1 | mg/tablet |
|---|---|---|
| | 'Compound X' | 100.0 |
| | β-lactam antibiotic | 100.0 |
| | Lactose | 77.5 |
| | Povidone | 15.0 |
| | Croscarmellose sodium | 12.0 |
| | Microcrystalline cellulose | 92.5 |
| | Magnesium stearate | 3.0 |
| | | 400.0 |

| (viii) | Tablet 2 | mg/tablet |
|---|---|---|
| | 'Compound X' | 20.0 |
| | β-lactam antibiotic | 20.0 |
| | Microcrystalline cellulose | 410.0 |
| | Starch | 50.0 |
| | Sodium starch glycolate | 15.0 |
| | Magnesium stearate | 5.0 |
| | | 520.0 |

| (ix) | Capsule | mg/capsule |
|---|---|---|
| | 'Compound X' | 10.0 |
| | β-lactam antibiotic | 10.0 |
| | Colloidal silicon dioxide | 1.5 |
| | Lactose | 465.5 |
| | Pregelatinized starch | 120.0 |
| | Magnesium stearate | 3.0 |
| | | 610.0 |

| (x) | Injection 1 | mg/ml |
|---|---|---|
| | 'Compound X' (free acid form) | 1.0 |
| | β-lactam antibiotic | 2.0 |
| | Dibasic sodium phosphate | 12.0 |
| | Monobasic sodium phosphate | 0.7 |
| | Sodium chloride | 4.5 |
| | 1.0 N Sodium hydroxide solution (pH adjustment to 7.0–7.5) | q.s. |
| | Water for injection | q.s. ad 1 mL |

| (xi) | Injection 2 | mg/ml |
|---|---|---|
| | 'Compound X' (free acid form) | 10.0 |
| | β-lactam antibiotic | 5.0 |
| | Monobasic sodium phosphate | 0.3 |
| | Dibasic sodium phosphate | 1.1 |
| | Polyethylene glycol 400 | 200.0 |
| | 01 N Sodium hydroxide solution (pH adjustment to 7.0–7.5) | q.s. |
| | Water for injection | q.s. ad 1 mL |

| (xii) | Aerosol | mg/can |
|---|---|---|
| | 'Compound X' | 20.0 |
| | β-lactam antibiotic | 20.0 |
| | Oleic acid | 10.0 |
| | Trichloromonofluoromethane | 5,000.0 |
| | Dichlorodifluoromethane | 10,000.0 |
| | Dichlorotetrafluoroethane | 5,000.0 |

The above formulations may be obtained by conventional procedures well known in the pharmaceutical art. "β-lactam antibiotic" can be any compound possessing antibiotic properties (e.g. amoxicillin, piperacillin, ampicillin, ceftizoxime, cefotaxime, cefuroxime, cephalexin, cefaclor, cephaloridine, or ceftazidime). Although specific quantities of "Compound X" and "β-lactam antibiotic" are shown in the above illustrative examples, it is to be understood that the compounds can be present in any ratio provided the final formulation possesses the desired antibiotic properties.

All publications, patents, and patent documents are incorporated by reference herein in their entirety. The invention has been described with reference to various specific and preferred embodiments and techniques. However, it should be understood that many variations and modifications may be made while remaining within the spirit and scope of the invention.

What is claimed is:

1. A compound of formula (I):

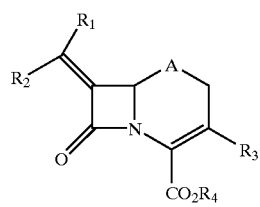

(I)

wherein:
R$_1$ and R$_2$ are each independently hydrogen, (C$_1$–C$_{10}$) alkyl, (C$_2$–C$_{10}$)alkenyl, (C$_2$–C$_{10}$)alkynyl, (C$_3$–C$_8$) cycloalkyl, (C$_1$–C$_{10}$)alkoxy, (C$_1$–C$_{10}$)alkanoyl, (C$_1$–C$_{10}$)alkanoyloxy, (C$_1$–C$_{10}$)alkoxycarbonyl, aryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

R$_3$ is hydrogen, bromo, iodo, aryl, heteroaryl, or —S(O)$_n$R$_h$;

R$_4$ is hydrogen;

A is thio, sulfinyl, or sulfonyl;

each n is independently 0, 1, or 2;

each R$_o$ is independently hydrogen, or (C$_1$–C$_{10}$)alkyl;

each R$_f$ and R$_g$ is independently hydrogen, (C$_1$–C$_{10}$)alkyl, (C$_1$–C$_{10}$)alkoxy, phenyl, benzyl, phenethyl, (C$_1$–C$_{10}$) alkanoyl, or —C(=O)NR wherein Q and the N atom to which it is attached forms a ring containing from 2–20 carbon atoms, optionally containing a nitrogen atom in the ring —NR$_6$—;

each R$_h$ is independently (C$_1$–C$_{10}$)alkyl, or phenyl;

R$_m$ is hydrogen or (C$_1$–C$_6$)alkyl; and

R$_m$ is hydrogen, and R$_p$ is NH$_2$, OH, (C$_2$–C$_{10}$)cycloalkyl, or —(C$_2$–C$_{10}$)alkyl-NH$_2$; or R$_m$ and R$_p$ together with the nitrogen to which they are attached form a piperidine, morpholine, thiomorpholine, pyrrolidine, or piperazine ring, wherein the piperazine is substituted at the 4-position with hydrogen or a (C$_1$–C$_{10}$)alkyl;

wherein any (C$_1$–C$_{10}$)alkyl, (C$_2$–C$_{10}$)alkenyl, (C$_2$–C$_{10}$) alkynyl, (C$_3$–C$_8$)cycloalkyl, (C$_1$–C$_{10}$)alkoxy, (C$_1$–C$_{10}$) alkanoyl, (C$_{10}$–C$_{10}$)alkanoyloxy, or (C$_1$–C$_{10}$) alkoxycarbonyl of R$_1$ or R$_2$ is optionally substituted with one or more, substituents independently selected from halo, hydroxy, cyano, cyanato, nitro, mercapto, oxo, aryl, heterocycle, (C$_2$–C$_6$)alkenyl, (C$_2$–C$_6$) alkynyl, (C$_1$–C$_6$)alkoxy, (C$_1$–C$_6$)alkanoyl, (C$_1$–C$_6$) alkanoyloxy, aryl(C$_1$–C$_6$)alkanoyloxy, halo(C$_1$–C$_6$) alkanoyloxy, heterocycle(C$_1$–C$_6$)alkanoyloxy, aryloxy, (heterocycle)oxy, (C$_3$–C$_8$)cycloalkyl, —COOR$_e$, —C(=O)NR$_f$R$_g$, —OC(=O)NR$_f$R$_g$, —NR$_h$R$_i$, or —S(O)$_n$R$_h$; and wherein any aryl is optionally substituted with one or more substituents independently selected from halo, hydroxy, cyano, trifluoromethyl, nitro, trifluoromethoxy, (C$_1$–C$_6$)alkyl, (C$_1$–C$_6$)alkanoyl, (C$_1$–C$_6$)alkanoyloxy, (C$_1$–C$_6$)alkoxycarbonyl, —COOR$_e$, —C(=O)NR$_f$R$_g$, —OC(=O)NR$_f$R$_g$, NR$_h$R$_i$, or —S(O)$_n$R$_h$; or a pharmaceutically acceptable salt thereof.

2. The compound of claim 1 wherein R$_1$ is aryl, heterocycle, or —COOR$_e$.

3. The compound of claim 1 wherein R$_{1i}$ is 2-pyridyl, or —COOR$_e$.

4. The compound of claim 1 wherein R$_2$ is hydrogen.

5. The compound of claim 1 wherein R$_3$ is hydrogen.

6. The compound of claim 1 wherein R$_3$ is bromo.

7. The compound of claim 1 wherein R$_3$ is iodo.

8. The compound of claim 1 wherein R$_3$ is aryl.

9. The compound of claim 1 wherein R$_3$ is phenyl.

10. The compound of claim 1 wherein R$_3$ is heteroaryl.

11. The compound of claim 1 wherein R$_3$ is 2-thienyl.

12. The compound of claim 1 wherein R$_3$ is S(O)$_n$R$_h$.

13. The compound of claim 1 wherein R$_3$ is S(O)$_2$R$_h$.

14. The compound of claim 13 wherein R$_h$ is methyl or phenyl.

15. The compound of claim 1 wherein R$_3$ is SR$_h$.

16. The compound of claim 15 wherein R$_h$ is methyl or phenyl.

17. The compound of claim 1 wherein R$_3$ is hydrogen, halo, aryl, heteroaryl, or —S(O)$_n$R$_h$.

18. The compound of claim 1 wherein A is sulfonyl.

19. The compound of claim 1 wherein A is sulfonyl; R$_1$ is 2-pyridyl, carboxy or tert-butoxy carbonyl; R$_2$ is hydrogen; and R$_3$ is hydrogen iodo, SPh, —SO$_2$Ph, SMe, —SO$_2$Me, or thiophene-2-yl; or a pharmaceutically acceptable salt.

20. A pharmaceutical composition comprising a compound of claim 1; or a pharmaceutically acceptable salt thereof; and a pharmaceutically acceptable carrier.

21. The composition of claim 20 further comprising a β-lactam antibiotic.

22. A method comprising inhibiting a β-lactamase by contacting said β-lactamase with an effective amount of a compound of claim 1.

23. A therapeutic method comprising inhibiting a Type-A, C, or D β-lactamase in a mammal in need of such therapy, by administering an effective inhibitory amount of a compound of claim 1.

24. A therapeutic method comprising enhancing the activity of a β-lactam antibiotic, by administering the β-lactam antibiotic to a mammal in need thereof, in combination with an effective β-lactamase inhibiting amount of a compound of claim 1.

25. A therapeutic method comprising treating a β-lactam resistant bacterial infection in a mammal, by administering to the mammal an effective amount of a β-lactam antibiotic, in combination with an effective β-lactamase inhibiting amount of a compound of claim 1.

26. A compound of formula (I):

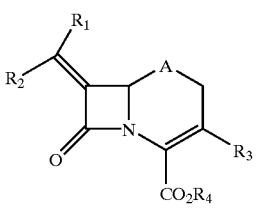

(I)

wherein:
R$_1$ and R$_2$ are each independently hydrogen, (C$_1$–C$_{10}$) alkyl, (C$_2$–C$_{10}$)alkenyl, (C$_2$–C$_{10}$)alkynyl, (C$_3$–C$_8$) cycloalkyl, (C$_1$–C$_{10}$)alkoxy, (C$_1$–C$_{10}$)alkanoyl, (C$_1$–C$_{10}$)alkanoyloxy, (C$_1$–C$_{10}$)alkoxycarbonyl, aryl, heteroaryl, heterocycle, halo, cyano, nitro, —COOR$_e$, —C(=O)NR$_f$R$_g$, —OC(=O)NR$_f$R$_g$, NR$_f$R$_g$, or —S(O)$_n$R$_h$;

R$_3$ is —Sn(R)$_3$ wherein each R is (C$_1$–C$_6$)alkyl;

R$_4$ is hydrogen or a protecting group;

A is thio, sulfinyl, or sulfonyl;

each n is independently 0, 1, or 2;

each $R_c$ is independently hydrogen, or $(C_1-C_{10})$alkyl;

each $R_f$ and $R_g$ is independently hydrogen, $(C_1-C_{10})$alkyl, $(C_1-C_{10})$alkoxy, phenyl, benzyl, phenethyl, $(C_1-C_{10})$alkanoyl, or —C(=Q)NQ; wherein Q and the N atom to which it is attached forms a ring containing from 2–20 carbon atoms, optionally containing a nitrogen atom in the ring, —$NR_e$;

each $R_h$ is independently $(C_1-C_{10})$alkyl, or phenyl;

$R_4$ is hydrogen or $(C_1-C_6)$alkyl; and wherein any $(C_1-C_{10})$alkyl, $(C_2-C_{10})$alkenyl, $(C_2-C_{10})$alkynyl, $(C_3-C_8)$cycloalkyl, $(C_1-C_{10})$alkoxy, $C_1-C_{10}$ alkanoyl, $(C_1-C_{10})$alkanoyloxy, or $(C_1-C_{10})$alkoxycarbonyl of $R_1$ or $R_2$ is optionally substituted with one or more, substituents independently selected from halo, hydroxy, cyano, cyanato, nitro, mercapto, oxo, aryl, heterocycle, $(C_2-C_6)$alkenyl, $(C_2-C_6)$alkynyl, $(C_1-C_6)$alkoxy, $(_1-C_6)$alkanoyl, $(C_1-C_6)$alkanoyloxy, aryl$(C_1-C_6)$alkanoyloxy, halo$(C_1-C_6)$alkanoyloxy, heterocycle$(C_1-C_6)$alkanoyloxy, aryloxy, (heterocycle)oxy, $(C_3-C_8)$cycloalkyl, —$COOR_e$, —C(=O)$NR_fR_g$, —OC(=O)$NR_fR_g$, —$NR_hR_i$, or —$S(O)_nR_h$; and wherein any aryl is optionally substituted with one or more substituents independently selected from halo, hydroxy, cyano, trifluoromethyl, nitro, trifluoromethoxy, $(C_1-C_6)$alkyl, $(C_1-C_6)$alkanoyl, $(C_1-C_6)$alkanoyloxy, $(C_1-C_6)$alkoxycarbonyl, —$COOR_e$, —C(O)$NR_fR_g$, —OC(=O)$NR_fR_g$, $NR_hR_i$, —$S(O)_nR_h$; or a pharmaceutically acceptable salt thereof.

* * * * *